(12) United States Patent
Barberich

(10) Patent No.: US 8,877,755 B2
(45) Date of Patent: Nov. 4, 2014

(54) DOPAMINE-AGONIST COMBINATION THERAPY FOR IMPROVING SLEEP QUALITY

(75) Inventor: Timothy J. Barberich, Concord, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 723 days.

(21) Appl. No.: 12/541,686

(22) Filed: Aug. 14, 2009

(65) Prior Publication Data

US 2010/0004251 A1    Jan. 7, 2010

Related U.S. Application Data

(62) Division of application No. 11/052,719, filed on Feb. 7, 2005, now abandoned.

(60) Provisional application No. 60/545,413, filed on Feb. 18, 2004.

(51) Int. Cl.
| | | |
|---|---|---|
| A61K 31/4985 | (2006.01) | |
| A61P 25/14 | (2006.01) | |
| A61K 31/137 | (2006.01) | |
| A61K 45/06 | (2006.01) | |
| A61K 31/425 | (2006.01) | |

(52) U.S. Cl.
CPC ............... *A61K 45/06* (2013.01); *A61K 31/137* (2013.01); *A61K 31/4985* (2013.01); *A61K 31/425* (2013.01)
USPC .......................................... 514/249; 514/373

(58) Field of Classification Search
USPC ................................................. 514/249, 373
See application file for complete search history.

(56) References Cited

U.S. PATENT DOCUMENTS

| | | | |
|---|---|---|---|
| 4,278,676 A | 7/1981 | Krogsgaard-Larsen | 424/256 |
| 4,419,345 A | 12/1983 | Wyatt | 424/153 |
| 4,505,914 A | 3/1985 | Metz et al. | 514/255 |
| 5,017,616 A | 5/1991 | Askanazi | |
| 5,430,029 A | 7/1995 | Biella et al. | 514/220 |
| 5,786,357 A | 7/1998 | Young et al. | 514/249 |
| 5,929,065 A | 7/1999 | Lancel | 514/188 |
| 6,211,173 B1 | 4/2001 | Fink-Jensen et al. | 514/213.1 |
| 6,231,594 B1 | 5/2001 | Dae | |
| 6,258,814 B1 | 7/2001 | Martin | 514/252.12 |
| 6,319,926 B1 | 11/2001 | Cotrel et al. | |
| 6,319,927 B1 | 11/2001 | Martin | 514/252.12 |
| 6,348,485 B1 | 2/2002 | Ohkawa et al. | 514/394 |
| 6,436,936 B1 * | 8/2002 | Young et al. | 514/249 |
| 6,444,673 B1 | 9/2002 | Cotrel et al. | |
| 6,864,257 B2 | 3/2005 | Cotrel et al. | |
| 7,125,874 B2 | 10/2006 | Cotrel et al. | |
| 7,381,724 B2 | 6/2008 | Cotrel et al. | |
| 7,465,729 B2 | 12/2008 | Wessel et al. | |
| 7,776,858 B2 | 8/2010 | Wessel et al. | |
| 2002/0019398 A1 | 2/2002 | Jerussi et al. | 514/249 |
| 2002/0143016 A1 | 10/2002 | Jerussi et al. | 514/249 |
| 2002/0165246 A1 | 11/2002 | Holman | |
| 2002/0193378 A1 | 12/2002 | Cotrel et al. | 514/249 |
| 2003/0119841 A1 | 6/2003 | Jerussi et al. | 514/249 |
| 2003/0166657 A1 | 9/2003 | Jerussi et al. | 514/249 |
| 2004/0067957 A1 * | 4/2004 | Jerussi et al. | 514/252.16 |
| 2004/0122104 A1 | 6/2004 | Hirsh et al. | 514/620 |
| 2004/0132826 A1 | 7/2004 | Hirsh et al. | 514/620 |
| 2004/0147521 A1 | 7/2004 | Jerussi et al. | 514/249 |
| 2005/0031688 A1 | 2/2005 | Ayala | 424/473 |
| 2005/0038042 A1 | 2/2005 | Codd et al. | 514/259.1 |
| 2005/0164987 A1 | 7/2005 | Barberich et al. | |
| 2005/0176680 A1 | 8/2005 | Lalji et al. | |

(Continued)

FOREIGN PATENT DOCUMENTS

| | | |
|---|---|---|
| EP | 1742624 B1 | 1/2010 |
| WO | WO 0025821 A1 * | 5/2000 |

(Continued)

OTHER PUBLICATIONS

Earley, "Restless Legs Syndrome", The New England Journal of Medicine. Boston: May 22, 2003. vol. 348, Iss. 21; p. 2103, 7 pgs.*

(Continued)

*Primary Examiner* — Sreeni Padmanabhan
*Assistant Examiner* — Sahar Javanmard
(74) *Attorney, Agent, or Firm* — Heslin, Rothenberg, Farley & Mesiti, P.C.

(57) ABSTRACT

The present invention generally relates to pharmaceutical compositions comprising a dopamine agonist and sedative agent. In a preferred embodiment, the dopamine agonist is optically pure (S)-didesmethylsibutramine. In a preferred embodiment, the sedative agent is optically pure (S)-zopiclone or optically pure (S)—N-desmethylzopiclone. In a preferred embodiment, the dopamine agonist is optically pure (S)-didesmethylsibutramine; and the sedative agent is optically pure (S)-zopiclone or optically pure (S)—N-desmethylzopiclone. The pharmaceutical compositions of the invention are useful in the treatment of restless-leg syndrome and periodic-limb-movement disorder, as well as various sleep disorders. In addition, the present invention relates to a method of treating a patient suffering from restless-leg syndrome, periodic-limb-movement disorder, a sleep abnormality, or insomnia, comprising coadministering a therapeutically effective amount of a dopamine agonist and a therapeutically effective amount of a sedative agent. In a preferred embodiment, the dopamine agonist is optically pure (S)-didesmethylsibutramine. In a preferred embodiment, the sedative agent is optically pure (S)-zopiclone or optically pure (S)—N-desmethylzopiclone. In a preferred embodiment, the dopamine agonist is optically pure (S)-didesmethylsibutramine; and the sedative agent is optically pure (S)-zopiclone or optically pure (S)—N-desmethylzopiclone.

2 Claims, 2 Drawing Sheets

(56) References Cited

U.S. PATENT DOCUMENTS

| | | |
|---|---|---|
| 2005/0215521 A1 | 9/2005 | Lalji et al. |
| 2005/0267176 A1 | 12/2005 | Barberich |
| 2007/0299055 A1 | 12/2007 | Lalji et al. |
| 2008/0293726 A1 | 11/2008 | Caron et al. |
| 2009/0111817 A1 | 4/2009 | Caron et al. |
| 2009/0111818 A1 | 4/2009 | Caron et al. |
| 2010/0280038 A1 | 11/2010 | Wessel et al. |

FOREIGN PATENT DOCUMENTS

| | | |
|---|---|---|
| WO | 00/56314 | 9/2000 |
| WO | 02/060424 | 8/2002 |
| WO | WO 03/022259 A1 | 3/2003 |
| WO | WO 2004/112786 A2 | 12/2004 |
| WO | WO2005/060968 | 7/2005 |
| WO | WO2005/063248 | 7/2005 |
| WO | WO2005/063297 | 7/2005 |
| WO | WO 2005/072715 A1 | 8/2005 |
| WO | 2005/079851 A2 | 9/2005 |
| WO | WO2005/097132 | 10/2005 |
| WO | WO2007/005961 | 1/2007 |
| WO | WO2007/005962 | 1/2007 |
| WO | WO2007/006003 | 1/2007 |
| WO | WO2007/005940 | 6/2007 |

OTHER PUBLICATIONS

International Search Report dated Apr. 4, 2006.
Lancel, M. et al., "Effect of the GABA, agonist gaboxadol on nocturnal sleep and hormone secretion in healthy elderly subjects," *Am. J. Physiol. Endocrinol. Metab.*, 281:E130-E137 (2001).
IPRP [from corresponding] International Application No. PCT/U52005/003937 dated Aug. 31, 2006.
Bennett et al. "GABA-mimetic drugs enhance apomorphine-induced contralateral turning in rates with unilateral nigrostriatal dopamine denervation: implications for the therapy of Parkinson's disease." Annals of Neurology, vol. 21, No. 1, p. 41-45 (1987).
Tachibana, Naoko. Restless legs syndrome (RLS), Suppl., Series of Nippon Rinsho Regional Syndrom No. 39. "Medical Syndromes of Psychiatry (II)—eating, sleeping, sexual and personality disorders, etc." Nippon Rinsho Corporation, p. 83-86 (Aug. 8, 2003).
Comella, CL. "Restless legs syndrome: Treatment with dopaminergic agents." Neurology, vol. 58, No. 4, Suppl. 1, p. S87-S92 (Feb. 26, 2002).
Krystal et al. "Sustained efficacy of eszopiclone over 6 months of nightly treatment: Results of a randomized, double-blind, placebo-controlled study in adults with chronic insomnia." Sleep, vol. 26, No. 7, p. 793-799 (Nov. 1, 2003).
Storustovu et al. "Gaboxadol: In vitro interaction studies with benzodiazepines and ethanol suggest functional selectivity." European Journal of Pharmacology, vol. 467, No. 1-3, p. 49-56 (Apr. 25, 2003).

\* cited by examiner

DOPAMINE-AGONIST COMBINATION THERAPY FOR IMPROVING SLEEP QUALITY

CROSS REFERENCE TO RELATED APPLICATIONS

This application is a divisional of copending U.S. application Ser. No. 11/052,719, filed Feb. 7, 2005. U.S. application Ser. No. 11/052,719 claimed benefit from U.S. Provisional Application 60/545,413, filed Feb. 18, 2004. The entire contents of each of the prior applications are incorporated herein by reference.

BACKGROUND OF THE INVENTION

Sleep is controlled by two biological processes, the homeostatic drive and the circadian rythym. The homestatic drive manifests itself as an increased drive for sleep. This drive for sleep accumulates across the period of wakefulness (typically daytime) and dissipates across the sleep period. The circadian rhythm of sleep-wake shows a biphasic curve with the greatest drive for sleep occurring between midnight and 5 AM, and between 2 PM and 4 PM. It is believed that major circadian influences are an alerting pulse in the evening and in the morning. It is the interaction of these processes which give rise to the 24-hour sleep schedule. For individuals with a usual sleep period of 11 PM to 7 AM, sleep onset in the evening occurs primarily as a function of homeostatic drive. After about four hours of sleep (at about 3 AM) homeostatic drive dissipates significantly and wakefulness begins to intrude into the sleep period. This propensity to increased wakefulness is further increased by the rise in the circadian alerting pulse at about 5 AM.

In terms of the pharmacological management of insomnia, two vulnerabilities have been recognized. The first is difficulty initially falling asleep, with the second being reawakening in the middle of the night. The formulations of the present invention address both of these issues by use of a particularly short acting sedative compound which has a single pulse at sleep onset, and a second pulse at the time of the decline in homeostatic processes and rise in the circadian pulse. The increase in plasma concentration from the dip at $T_{min}$ value to that of $T_{max2}$ has been found to be particularly beneficial in preventing subsequent awakening of the patient. Much like the initial plasma concentration pulse from time of administration to $T_{max1}$, which results in the patient falling asleep, the pulse from the concentration at $T_{min}$ to $T_{max2}$ has been found to be particularly beneficial for sleep maintenance. To this end, it is believed that this increase in plasma concentration is more beneficial than merely maintaining a constant plasma concentration of the sedative compound. For example, by having the plasma concentration dip between $T_{max1}$ and $T_{max2}$ the patient is exposed to a lower overall dosage, thereby decreasing subsequent effects, such as unwanted hangover effect. In addition, a lower plasma concentration at $T_{min}$ decreases incidents of nighttime falls and/or amnesia, particularly in the elderly.

Many physiological functions are characterized by diurnal rhythms, in which levels of circulating hormones, catecholamines and other compounds fluctuate during the day and/or night. Certain medical disorders, such as insomnia, are associated with abnormalities in these rhythms. The time, within a 24 hour period, of administration of drugs for the prevention and treatment of such disorders can be a critical factor in determining efficacy of the therapy.

The term "insomnia" refers to the perception of inadequate or non-restful sleep by a patient. Insomnia is a frequent complaint, reported by 32% of the adult population surveyed in the Los Angeles area (Bixler et al, Amer. Journal of Psychiatry 136:1257-1262, 1979), and 13% of the population surveyed in San Marino, Italy (Lugaresi et al., Psychiatric Annals 17:446-453, 1987). Fully 45% of the surveyed adult population of Alachua County, Florida, reported trouble getting to sleep or staying asleep (Karacan et al., Social Science and Medicine 10:239-244, 1976). The prevalence of insomnia has also been shown to be related to the age and sex of the individuals, being higher in older individuals and in females.

Early treatments for insomnia commonly employed central nervous system (CNS) depressants, such as barbiturates. These compounds are typically long acting (on the order of 8-50 hours) due to long terminal half-lives, and have a well-known spectrum of side effects, including lethargy, confusion, depression and next day hangover effects. In addition, chronic use has been associated with a high potential for addiction involving both physical and psychological dependence.

During the 1980s, the pharmaceutical treatment of insomnia shifted away from barbiturates and other CNS depressants toward the benzodiazepine class of sedative-hypnotic agents. This class of compounds produces a calming effect that results in a sleep-like state in humans and animals, with a greater safety margin than prior hypnotics. The therapeutic actions of benzodiazepines are believed to be mediated by binding to a specific receptor on benzodiazepine GABA complexes in the brain. As a result of this binding, synaptic transmission is altered at neurons containing the benzodiazepine GABA complex. The clinical usefulness of different benzodiazepine hypnotics relates largely to their pharmacokinetic differences with regard to this binding and, in particular, to the half-lives of the parent compound and its active metabolites. However, many benzodiazepines possess side effects that limit their usefulness in certain patient populations. These problems include synergy with other CNS depressants (especially alcohol), the development of tolerance upon repeat dosing, rebound insomnia following discontinuation of dosing, hangover effects the next day and impairment of psychomotor performance and memory. Next day sleepiness and memory impairment, which can include amnesia for events occurring prior to and after drug administration, is of particular concern in the elderly whose cognitive functions may already be impaired by the aging process.

More recent treatments for insomnia have used non-benzodiazepine compounds, which show an improved side-effect profile over the benzodiazepine class of sedative-hypnotics. The first of these agents to be approved by the United States Food and Drug Administration (FDA) for marketing in the United States was AMBIEN® (zolpidem), which is based on the imidazopyridine backbone (see U.S. Pat. Nos. 4,382, 938 and 4,460,592). In addition to AMBIEN®, another compound known as SONATA® (zaleplon), which is a pyrazolopyrimidine-based compound (see U.S. Pat. No. 4,626,538), was recently approved by the FDA. Other non-benzodiazepine compounds and/or methods for making or using the same have also been reported (see, e.g., U.S. Pat. Nos. 4,794, 185, 4,808,594, 4,847,256, 5,714,607, 4,654,347; 5,538,977, 5,891,891). Attempts have also been disclosed to provide controlled-release dosage forms, particularly in the context of zolpidem and salts thereof (see WO 00/33835 and EP 1 005 863 A1).

Restless-legs syndrome ("RLS") is a movement disorder that can disrupt sleep for a substantial number of people. RLS is characterized by uncomfortable sensations in the legs, which are worse during periods of inactivity, rest, or while sitting or lying down. Patients with the disorder describe the sensations as pulling, drawing, crawling, wormy, boring, tingling, pins and needles, prickly, itchy, and sometimes painful sensations that are usually accompanied by an overwhelming urge to move. As a result of problems both while awake and while attempting sleep or during sleep, people with RLS may have difficulties with their job, social life, and recreational activites. RLS is reasonably common and always distressing.

Accordingly, there is a need in the art for sedative-dopamine agonist compositions that induce and maintain sleep as single dose nocturnal formulations. The present invention fulfills this need and further provides other related advantages.

SUMMARY OF THE INVENTION

The present invention generally relates to pharmaceutical compositions comprising a dopamine agonist and sedative agent. In a preferred embodiment, the dopamine agonist is optically pure (S)-didesmethylsibutramine. In a preferred embodiment, the sedative agent is optically pure (S)-zopiclone or optically pure (S)—N-desmethylzopiclone. In a preferred embodiment, the dopamine agonist is optically pure (S)-didesmethylsibutramine; and the sedative agent is optically pure (S)-zopiclone or optically pure (S)—N-desmethylzopiclone. The pharmaceutical compositions of the invention are useful in the treatment of restless-leg syndrome and periodic-limb-movement disorder, as well as various sleep disorders. In addition, the present invention relates to a method of treating a patient suffering from restless-leg syndrome, periodic-limb-movement disorder, a sleep abnormality, or insomnia, comprising coadministering a therapeutically effective amount of a dopamine agonist and a therapeutically effective amount of a sedative agent. In a preferred embodiment, the dopamine agonist is optically pure (S)-didesmethylsibutramine. In a preferred embodiment, the sedative agent is optically pure (S)-zopiclone or optically pure (S)—N-desmethylzopiclone. In a preferred embodiment, the dopamine agonist is optically pure (S)-didesmethylsibutramine; and the sedative agent is optically pure (S)-zopiclone or optically pure (S)—N-desmethylzopiclone.

DETAILED DESCRIPTION OF THE INVENTION

Figure 1:
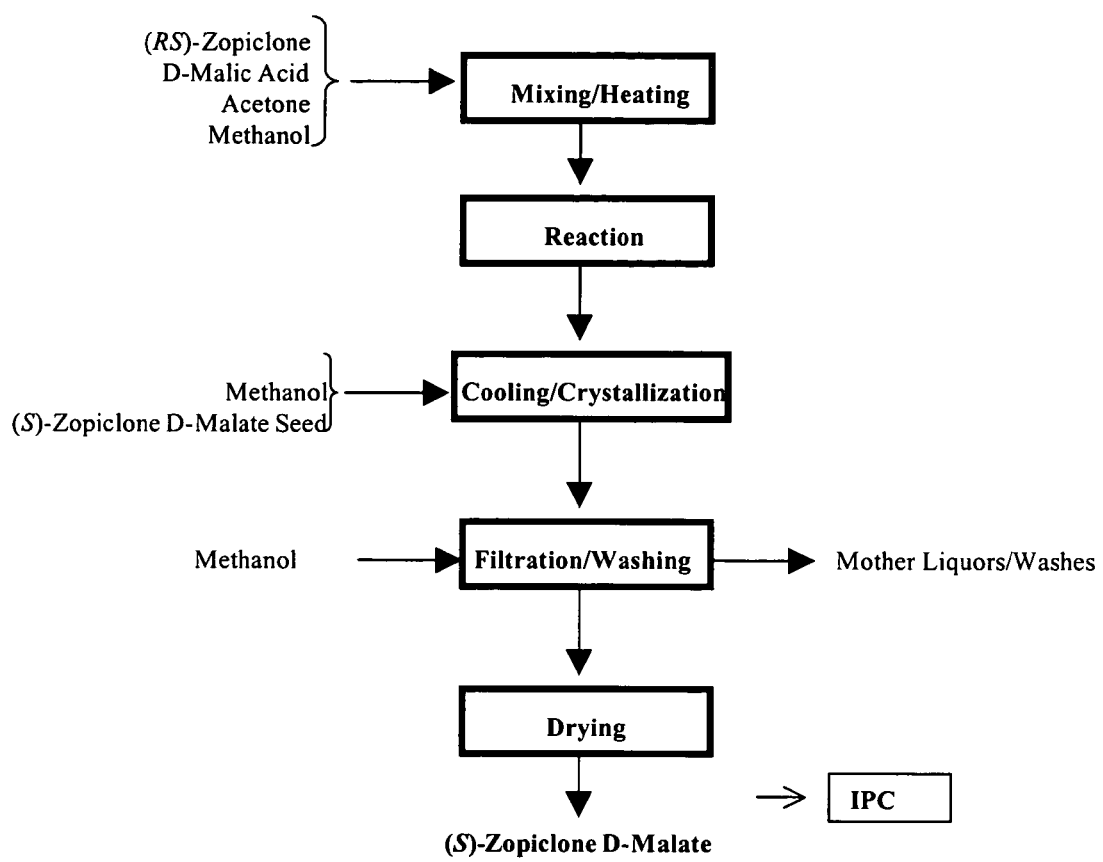
FIG. 1 depicts a schematic diagram of a method for preparing optically pure (S)-zopiclone D-malate (IPC=in-process control testing).

The present invention relates generally to pharmaceutical compositions containing two or more active agents that when taken together improve the quality of sleep for a patient. In certain embodiments, the present invention relates to a pharmaceutical composition comprising a dopamine agonist and a sedative agent. In a preferred embodiment, the present invention relates to a pharmaceutical composition comprising optically pure (S)-didesmethylsibutramine. In a preferred embodiment, the sedative agent is optically pure (S)-zopiclone or optically pure (S)—N-desmethylzopiclone. Another aspect of the present invention relates to a method of treating a patient suffering from restless-leg syndrome, periodic-limb-movement disorder, or a sleep disorder, comprising the step of administering to said patient a therapeutically effective dose of pharmaceutical composition of the present invention. In certain embodiments, the present invention relates to the aforementioned method, wherein said pharmaceutical composition comprises a dopamine agonist and sedative agent. In a preferred embodiment, the present invention relates to the aforementioned method, wherein said pharmaceutical composition comprises optically pure (S)-didesmethylsibutramine. In a preferred embodiment, the sedative agent is optically pure (S)-zopiclone or optically pure (S)—N-desmethylzopiclone. In a preferred embodiment, said pharmaceutical composition comprises optically pure (S)-didesmethylsibutramine; and the sedative agent is optically pure (S)-zopiclone or optically pure (S)—N-desmethylzopiclone.

Sleep Difficulties and Insomnia

Several epidemiologic studies suggest that 10% to 15% of adults suffer from chronic insomnia, and an additional 25% to 35% have transient or occasional insomnia (Roth T. *Int. J. Clin. Pract. Suppl.* 2001, 3-8).

The National Sleep Foundation's 2002 Sleep in America survey assessed the occurrence of four symptoms of insomnia in adults in the United States: difficulty falling asleep; waking a lot during the night; waking up too early and not being able to get back to sleep; and waking up feeling unrefreshed. In the survey, 58% of the respondents reported experiencing at least one of these symptoms a few nights a week or more, and 35% reported difficulties every night or almost every night within the past year (National Sleep Foundation. 2002 Sleep in America Poll. Washington, D.C.: WB & A Market Research, 2002, 1-43). In addition, of those reporting insomnia symptoms at least a few nights a week, 40% reported feeling unrefreshed upon awakening, 36% reported being awake a lot during the night, 25% reported difficulty falling asleep, and 24% reported waking up too early and being unable to fall back asleep.

The major types of insomnia are often described as primary and secondary insomnia (as in the American Psychiatric Association's *Diagnostic and Statistical Manual of Mental Disorders*, Text Revision. 4th ed. Washington, D.C.: American Psychiatric Publishing, Inc, 2000 [DSM]), chronic versus acute/transient insomnia, intrinsic versus extrinsic insomnia (as in the International Classification of Sleep Disorders [ICSD]), and sleep-onset versus sleep maintenance (Diagnostic Classification Steering Committee. International Classification of Sleep Disorders (ICSD): Diagnostic and Coding Manual. Rochester, Minn.: American Sleep Disorders Association, 1990). Many patients with sleep disturbance will fall into more than one of these categories or will have unspecified dissatisfaction with the quality of their sleep (Roth T. *Int. J. Clin. Pract. Suppl.* 2001, 3-8). The fourth edition of the DSM (DSM-IV) defines insomnia as difficulties in sleep onset (or initiation), difficulties in sleep maintenance, or sleep that is nonrestorative.

Chronic insomnia may result from several different sources (Rajput et al., *Am. Fam. Physician*, 1999, 60:1431-1438). Patients with chronic insomnia can often have several sleep complaints simultaneously and experience a range of sleep disturbances, including prolonged latency to sleep onset, increased time awake during the sleep period, and reduced total sleep time (Benca R M, *J. Clin. Psychiatry*, 2001, 62 Suppl 10:33-38).

Sleep maintenance problems may take several forms, including frequent awakenings, an increase in time spent awake after initially falling asleep (wake time after sleep onset, or WASO, which is a robust measure of sleep maintenance), sleep fragmentation (transient microarousals appearing on an EEG but not necessarily involving full wakefulness), and unrefreshing sleep. Of these, WASO is a particularly sensitive measure of sleep improvement. WASO may include a number of microarousals, as well as all periods of full wakefulness, and thus increases in WASO of only a few minutes may be indicative of substantially improved sleep continuity.

The severity of insomnia can be directly correlated to severity of next-day functional impairment. There is also strong evidence that, compared with patients without insomnia, patients with chronic insomnia experience a subjective deterioration in waking behaviors and psychosocial functioning, including impaired memory, concentration, ability to accomplish tasks, and enjoyment of interpersonal relationships (Roth et al., *Sleep*, 1999, 22 Suppl 2:S354-S358).

Sleep maintenance problems may cause decreases in next-day functioning. Bonnet studied healthy volunteers with normal sleep habits and found that, with increasing periods of induced arousal or insomnia during the night, residual effects of next-day performance on evaluations of vigilance, reaction time, sleepiness, and other measures experienced corresponding decreases (Bonnet M H, *Physiol. Behav.*, 1989, 45:1049-1055).

Dopamine Agonists

Amantadine

Amantadine is a cycloalkylanine used to treat Parkinson's Disease, Influenca A, and drug-induced extrapyramidal reactions. Procedures for the preparation of amantadine are described in U.S. Pat. No. 3,1452,180 and Stetter et al. *Ber.* 1960, 93, 226. The pharmacological properties are described in Vernier et al. *Toxicol. Appl. Pharmacol.* 1969, 15, 642 and R. Dolin et al. *N. Engl. J. Med.* 1982, 307, 580. For a comprehensive description see J. Kirschbaum *Anal. Profiles Drug Subs.* 1983, 12, 1-36. The hydrochloride salt of amantadine is marketed under the brandname MANTADINE for the treatment of herpes simplex infections, influenza A infection, and Parkinson's Disease. Amantadine has the chemical name tricyclo[3.3.1.1$^{3,7}$]decan-1-amine and the structure is presented below.

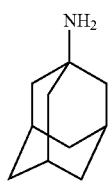

The size of a prophylactic or therapeutic dose of amantadine in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 20 mg to about 500 mg. Preferably, a daily dose range should be between about 40 mg to about 350 mg. Most preferably, a daily dose range should be between about 60 mg to about 250 mg. In certain embodiments, the daily dose range should be about 100, 150, or 200 mg. In managing the patient, the therapy may be initiated at a lower dose, perhaps about 50 mg to about 75 mg and increased up to about 125 mg or higher depending on the patient's global response.

Apomorphine

Apomorphine is a morphine derivative that has been used or considered for use in the treatment of a variety of disorders. Apomorphine is a synthetic opiate obtained by treating morphine with concentrated hydrochloric acid as described in Small et al. *J. Org. Chem.* 1940, 5, 344 or by heating morphine with zinc chloride as described in Mayer *Ber.* 1871, 4, 121. Procedures for the synthesis of racemic apomorphine are described in U.S. Pat. No. 3,717,639 and J. L. Neumeyer et al. *J. Chem. Chem.* 1973, 16, 1223. Procedures for the synthesis of the individual enantiomers has been described by V. J. Ram and J. L. Neumeyer in *J. Org. Chem.* 1981, 46, 2830. The pharmacological properties have been described in DiChiara, G.; Gesssa, G. L.; *Adv. Pharmacol. Chemother.* 1978, 15, 87. For a review of apomorphine see Muhtadi, R. J.; Hiffiawy, M. S. *Analytical Profiles of Drug Substances*, Vol. 20, K. Florey, Ed. (Academic Press, New York, 1991) pp. 121-166. The chemical name of apomorphine is (R)-5,6,6a,7-tetrahydro-6-methyl-4H-dibenzo-[de,g]quinoline-10,11-diol and the structure is presented below.

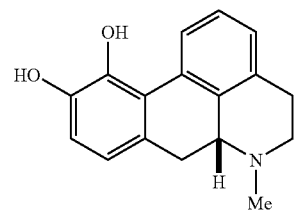 [SMILES: CN1CCc2cccc3c2[C@H]1Cc1ccc(O)c(O)c1-3]

Acute and subacute testing of apomorphine HCl has been reported in studies with daily doses ranging to over 300 milligrams per kilogram (mg/kg) in lower vertebrates (amphibian and birds), and to 10 mg/kg in higher mammals (primates). In mammals, it appears doses of apomorphine HCl are tolerated up to about 13 mg/kg in a single bolus subcutaneous injection. Doses at or above this amount have been reported lethal in mouse, although, the LD$_{50}$ is considerably higher (>50 mg/kg) in this species. Continuous infusion of apomorphine has been tolerated and reported to doses of 420 μg/kg/hr for 14 days. Larger doses (1,500 μg/kg/hr were found to be minimally lethal over the course of the 14 day study). In primates, multiple doses of apomorphine HCl have been administered for up to four days at 100-400 μg/kg without major adverse effects.

Administration of large doses of apomorphine to mammals such as humans, dogs and the like usually results in nausea and vomiting, and is believed to be due to the action of apomorphine on the chemoreceptor trigger zone (CTZ) of the medulla oblongata, a structure of the mammalian central nervous system. It is believed that additional chemoreceptors triggering emesis are present in the gastrointestinal tract as well. In sensitive patients experiencing nausea, the onset of nausea can be obviated or delayed by delivering apomorphine at a controlled dissolution rate so as to provide circulating serum levels and midbrain tissue levels of apomorphine less than 5.5 ng/mL. When apomorphine is administered at or near the higher amounts of the aforementioned dosage range, the likelihood of the onset of nausea can be reduced by concurrent administration of a ganglionic agent (inhibitor of ganglionic response and anti-emetic agent) such as nicotine or lobeline sulfate.

The size of a prophylactic or therapeutic dose of apomorphine in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.5 mg to about 75 mg. Preferably, a daily dose range should be between about 2 mg to about 30 mg. Most preferably, a daily dose range should be between about 2 mg to about 10 mg. In certain embodiments, the daily dose range should be about 4, 6, or 8 mg. In managing the patient, the therapy may be initiated at a lower dose, perhaps about 1 mg to about 1.5 mg and increased up to about 3 mg or higher depending-on the patient's global response.

Bromocriptine (PARLODEL®)

Bromocriptine is a derivative of the ergotoxin group of ergot alkaloids and is a dopamine-receptor agonist. Procedures for the synthesis of bromocriptine are described in U.S. Pat. Nos. 3,752,814 and 3,752,888. The pharmacological properties and therapeutic uses are reviewed in Fluckiger *Triangle (Engl. Ed.)* 1975, 14, 153 and Ho, K. Y.; Thorner, M. O. *Drugs* 1988, 36, 67. The methanesulfonate salt of bromocriptine is marketed under the tradename PARLODEL®. Bromocriptine has the chemical name (5α)-2-bromo-12'-hydroxy-2'-(1-methylethyl)-5'-(2-methylpropyl)ergotaman-3', 6',18-trione and the structure is presented below.

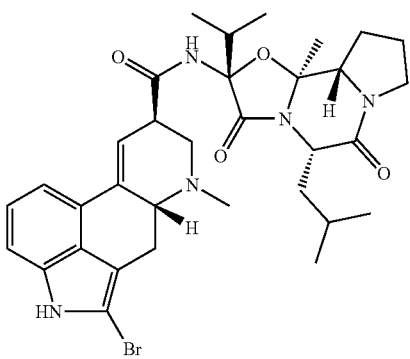

The size of a prophylactic or therapeutic dose of bromocriptine in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.5 mg to about 75 mg. Preferably, a daily dose range should be between about 1 mg to about 30 mg. Most preferably, a daily dose range should be between about 1 mg to about 10 mg. In certain embodiments, the daily dose range should be about 2, 4, 6, or 8 mg. In managing the patient, the therapy may be initiated at a lower dose, perhaps about 1 mg to about 1.5 mg and increased up to about 3 mg or higher depending-on the patient's global response.

Cabergoline (DOSTINIEX®)

Cabergoline is a pharmacologically unique dopamine receptor antagonist because it is a full $D_2$ agonist with only partial $D_1$ activity. Procedures for the synthesis of cabergoline are described in U.S. Pat. No. 4,526,892 and by E. Brambilla et al. in *Eur. J. Med. Chem.* 1989, 24, 421. Procedures for the preparation of different crystalline forms of cabergoline are described in U.S. Pat. Nos. 6,680,327 and 6,673,806. Cabergoline has been used in the treatment of Restless-leg Syndrome (RLS) and Parkinson's disease. See U.S. Pat. No. 6,114,326 and J. E. Ahlskog et al. *Clin. Neuropharmacol.* 1996, 19, 202-212. Cabergoline is a good therapeutic agent for treating patents with RLS because it has a long half life (upto 65 hr). Cabergoline has the chemical name 1-[(6-allylergolin-8β-yl)-carbonyl]-1-[3-(dimethylamino)propyl]-3-ethylurea and the structure is presented below.

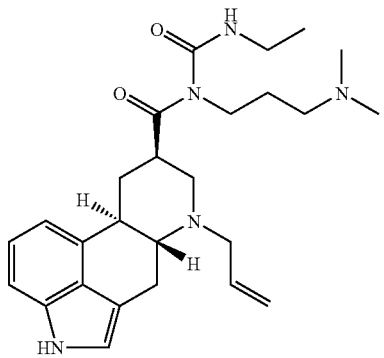 [SMILES: C=CCN1C[C@H](C(=O)N(CCCN(C)C)C(=O)NCC)C[C@@H]2c3cccc4[nH]cc(c34)C[C@H]21]

The size of a prophylactic or therapeutic dose of cabergoline in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.1 mg to about 60 mg. Preferably, a daily dose range should be between about 0.1 mg to about 20 mg. Most preferably, a daily dose range should be between about 0.1 mg to about 10 mg. In certain embodiments, the daily dose range should be about 1, 2, 4, 6, or 8 mg. In managing the patient, the therapy may be initiated at a lower dose, perhaps about 0.1 mg to about 0.5 mg and increased up to about 2 mg or higher depending-on the patient's global response.

Carmoxirole

Carmoxirole is an indole derivative that is a selective dopamine $D_2$-receptor agonist. Procedures for the synthesis of carmoxirole are described in U.S. Pat. No. 5,256,673 and Bottcher, H.; Gericke, R. *Ann.* 1988, 749. The pharmacological properties of carmoxirole are described in G. Haeusler et al. *Eur. Heart J.* 1992, 13 (Suppl. D), 129 and W. Meyer et al. *Eur. Heart J.* 1992, 13 *(Suppl. D)*, 121. The dose, and perhaps the dose frequency, will also vary according to the age, body weight, and response of the individual patient. In general, the total daily dose ranges, for the conditions described herein, is from about 1 mg to about 900 mg. Preferably, a daily dose range should be between about 10 mg to about 200 mg. Carmoxirole has the chemical name 3-[4-(3,6-dihydro-4-phenyl-1(2H)-pyridinyl)butyl]-1H-indole-5-carboxylic acid and the structure is presented below.

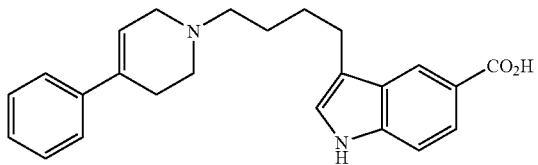 [SMILES: O=C(O)c1ccc2[nH]cc(CCCCN3CC=C(c4ccccc4)CC3)c2c1]

(S)-Didesmethylsibutramine (S)-Didesmethylsibutramine is an active metabolite of sibutramine. Procedures for the synthesis of didesmethylsibutramine are described in U.S. Pat. No. 6,610,887. The behavior effects of didesmethylsibutramine have been described by Glick S. D. and coworkers. Glick S. D., et al. *Eur. J. Pharmacol.* 2000, 397, 93-102. (S)-Didesmethylsibutramine has the chemical name 1-[1-(4-chlorophenyl)cyclobutyl]-3-methyl-butylamine and the structure is presented below.

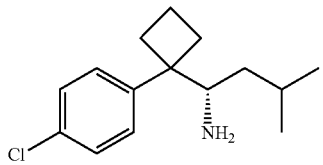 [SMILES: CC(C)C[C@H](N)C1(c2ccc(Cl)cc2)CCC1]

Racemic didesmethylsibutramine can be prepared by methods known to those of ordinary skill in the art. See, e.g., U.S. Pat. No. 4,806,570, which is incorporated herein by reference; *J. Med. Chem.*, 2540 (1993) (tosylation and azide replacement); Butler, D., *J. Org. Chem.*, 36:1308 (1971) (cycloalkylation in DMSO); *Tetrahedron Lett.*, 155-58 (1980) (Grignard addition to nitrile in benzene); *Tetrahedron Lett.*, 857 (1997) (OH to azide); and Jeffery, J. E., et al. , *J. Chem. Soc. Perkin. Trans* 1, 2583 (1996).

Racemic didesmethylsibutramine can be prepared from racemic sibutramine or desmethylsibutramine, as can optically pure forms of the compound. Optically pure enantiomers of didesmethylsibutramine can be prepared using techniques known in the art. A preferred technique is resolution by fractional crystallization of diastereomeric salts formed with optically active resolving agents. See, e.g., "Enantiomers, Racemates and Resolutions," by J. Jacques, A. Collet, and S. H. Wilen, (Wiley-Interscience, New York, 1981); S. H. Wilen, A. Collet, and J. Jacques, *Tetrahedron*, 2725 (1977); E. L. Eliel *Stereochemistry of Carbon Compounds* (McGraw-Hill, N.Y., 1962); and S. H. Wilen *Tables of Resolving Agents and Optical Resolutions* 268 (E. L. Eliel ed., Univ. of Notre Dame Press, Notre Dame, Ind., 1972).

Because didesmethylsibutramine is a basic amine, diastereomeric salts of the compound that are suitable for separation by fractional crystallization are readily formed by addition of optically pure chiral acid resolving agents. Suitable resolving agents include, but are not limited to, optically pure tartaric, camphorsulfonic acid, mandelic acid, and derivatives thereof. Optically pure isomers of didesmethylsibutramine can be recovered either from the crystallized diastereomer or from the mother liquor, depending on the solubility properties of the particular acid resolving agent employed and the particular acid enantiomer used. The identity and optical purity of the particular didesmethylsibutramine so recovered can be determined by polarimetry or other analytical methods.

Racemic and optically pure didesmethylsibutramine are preferably synthesized directly by methods such as those disclosed by Jeffery, J. E., et al., *J. Chem. Soc. Perkin. Trans* 1, 2583 (1996).

A preferred method of directly synthesizing racemic didesmethylsibutramine comprises the reaction of CCBC with a compound of formula i-BuMX, wherein X is Br or I and M is selected from the group consisting of Li, Mg, Zn, Cr, and Mn. Preferably, the compound is of the formula i-BuMgBr. The product of this reaction is then reduced under suitable reaction conditions.

The enantiomers of didesmethylsibutramine can be resolved by the formation of chiral salts, as described above. Preferred chiral acids used to form the chiral salts include, but are not limited to, tartaric acid. Preferred solvent systems include, but are not limited to, acetonitrile/water/methanol and acetonitrile/methanol.

The size of a prophylactic or therapeutic dose of didesmethylsibutramine in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 900 mg. Preferably, a daily dose range should be between about 1 mg to about 500 mg. Most preferably, a daily dose range should be between about 1 mg to about 100 mg. In certain embodiments, the daily dose range should be about 5, 10, 25, 50, or 75 mg.

Dopexamine

Dopexamine is a dopamine-receptor agonist and $\beta_2$-adrenoreceptor agonist. Procedures for the synthesis of depexamine are described in European Patent Application 72,061. The pharmacological properties of dopexamine are described in *Am. J. Cardiol.* 1988, 62, 1C-88C. In general, the total daily dose ranges, for the conditions described herein, is from about 1 mg to about 900 mg. Preferably, a daily dose range should be between about 10 mg to about 200 mg. Dopexamine has the chemical name 4-[2-[[6-[(2-phenylethyl)amino]hexyl]amino]ethyl]-1,2-benzenediol and the structure is presented below.

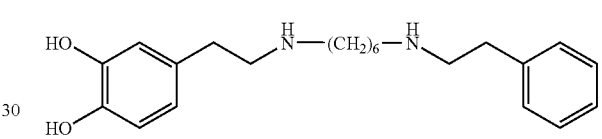

Fenoldopam

Fenoldopam is a dopamine $D_1$-receptor agonist. Procedures for the preparation of fenoldopam are described in U.S. Pat. No. 4,197,297 and J. Weinstock et al. *J. Med. Chem.* 1980, 23, 973. The pharmacological properties are described in R. M. Stote et al. *Clin. Pharmacol. Ther.* 1983, 34, 309 and G. S. Francis et al. *Am. Heart J.* 1988, 116, 473. Among the various known salts of fenoldopam, fenoldopam 4',8-bis-hydrogen sulfate is a useful prodrug to obtain extended dopaminergic activity. See U.S. Pat. No. 4,600,714. Fenoldopam has the chemical name 6-chloro-2,3,4,5-tetrahydro-1-(4-hydroxyphenyl)-1H-3-benzazepine-7,8-diol and the structure is presented below.

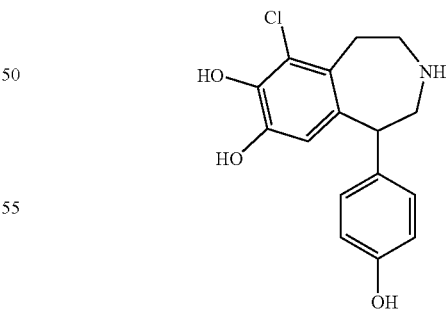

Fenoldopam is a dopamine agonist that causes peripheral vasodilation via stimulation of dopamine type-1 receptors. The drug is currently administered under the brandname CORLOPAM® as an intravenous infusion of racemic fenoldopam mesylate and is typically used in clinical situations where, either due to underlying disease or induced by trauma or a medical procedure, an elevation in blood pressure occurs requiring immediate correction. In these situations, fenoldopam can be given at a dose of between about 0.01-1.6 µg/kg/min for up to 48 hours to achieve a dose-dependent steady-state plasma concentration in about 20 minutes.

In addition to producing a decrease in blood pressure, fenoldopam also causes renal vasodilation, diuresis and natriuresis. Intravenous infusion of therapeutic dosages of fenoldopam increases renal blood flow and decreases renal vascular resistance while maintaining glomerular filtration rate and increasing creatinine clearance, urinary flow and excretion of sodium and potassium. See Brogden, R. N.; Markham, A. *Drugs* 1997, 54(4), 634-650. These beneficial effects of fenoldopam on renal function are particularly desirable for hypertensive patients with compromised renal function.

However, the antihypertensive and renal effects of fenoldopam are often short lasting, due to a high first-pass metabolism via sulfation and glucuronidation of the 3,4-dihydroxy benzene ring of fenoldopam. See Lokhandwala, M. F. *Drug Development Research* 1987, 10, 123-134. The average clearance (CL) and half-life ($t_{1/2}$) of racemic fenoldopam are 2.6 L/min and 4.6 min, respectively. Because of the high first-pass metabolism and short half-life, it is difficult to maintain a therapeutically effective concentration via oral administration and for a continuous therapeutic effect frequent dosing, i.e., intravenous infusion, is often required.

The size of a prophylactic or therapeutic dose of fenoldapam in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 500 mg. Preferably, a daily dose range should be between about 5 mg to about 250 mg. Most preferably, a daily dose range should be between about 10 mg to about 170 mg. In certain embodiments, the daily dose range should be about 50, 75, 100, 125, or 150 mg. In managing the patient, the therapy may be initiated at a lower dose, perhaps about 5 mg to about 15 mg and increased up to about 25 mg or higher depending-on the patient's global response.

Ibopamine

Ibopamine has the chemical name 2-methylpropanioc acid 4-[2-(methylamino)ethyl]-1,2-phenylene ester. Procedures for the synthesis of ibopamine are described in U.S. Pat. No. 4,218,470. The pharmacological properties are described in G. F. Melloni et al. *Curr. Ther. Res.* 1979, 25, 406 and Henwood, J. M.; Todd, P. A. *Drugs* 1988, 36, 11-31. The hydrochloride salt of ibopamine is marketed under the brandname INOPAMIL®.

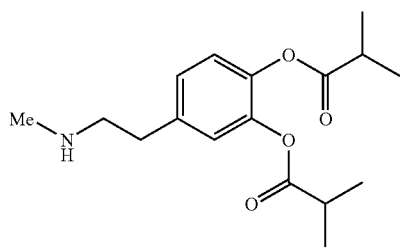 [SMILES: CNCCc1ccc(OC(=O)C(C)C)c(OC(=O)C(C)C)c1]

The size of a prophylactic or therapeutic dose of ibopamine in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 500 mg. Preferably, a daily dose range should be between about 50 mg to about 250 mg. Most preferably, a daily dose range should be between about 75 mg to about 150 mg. In certain embodiments, the daily dose range should be about 100 or 125 mg. In managing the patient, the therapy may be initiated at a lower dose, perhaps about 85 mg to about 90 mg and increased up to about 110 mg or higher depending-on the patient's global response.

Lergotrile

Lergotrile has the chemical name 2-chloro-6-methylergoline-8β-acetonitrile.

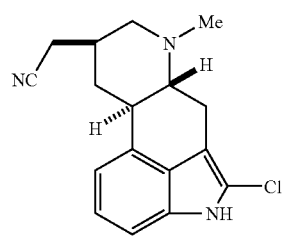

Lergotrile has been administered to humans to suppress the secretion of prolactin by the pituitary gland and to patients suffering from Parkinson's disease. In addition, Lergotrile has also been used to reduce blood pressure. See U.S. Pat. No. 4,298,611. In general, the total daily dose ranges, for the conditions described herein, is from about 1 mg to about 900 mg. Preferably, a daily dose range should be between about 10 mg to about 200 mg.

Lisuride (DOPERGIN®)

Lisuride is a dopamine $D_2$-receptor antagonist that can be used in the treatment of Parkinson's disease, migraine headache, urticaria, hypertension, and allergic conditions. Procedures for the preparation of lisuride are described in U.S. Pat. No. 3,953,454 and Zikan, V.; Semonsky, M. Coll. *Czech. Chem. Commun.* 1960, 25, 1922. The pharmacological properties of lisuride are described in Votava, Z.; Lamplova, E. *Physiol. Bohemoslov.* 1963, 12, 37. The maleate salt of lisuride is marketed under the tradename DOPERGIN® for the treatment of Parkinson's Disease. Lisuride has the chemical name N-(D-6-methyl-8-isoergolenyl)-N',N'-diethylurea and the structure is presented below.

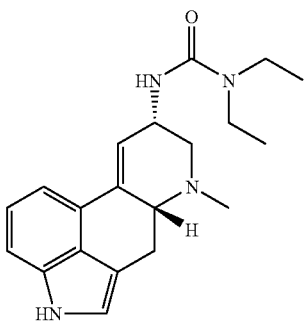 [SMILES: CCN(CC)C(=O)N[C@H]1C=C2c3cccc4[nH]cc(c34)C[C@H]2N(C)C1]

The size of a prophylactic or therapeutic dose of lisuride in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.1 mg to about 75 mg. Preferably, a daily dose range should be between about 0.1 mg to about 20 mg. Most preferably, a daily dose range should be between about 0.1 mg to about 5 mg. In certain embodiments, the daily dose range should be about 0.2, 0.5, 1, 2, 3, or 4 mg. In managing the patient, the therapy may be initiated at a lower dose, perhaps about 0.1 mg to about 0.3 mg and increased up to about 1 mg or higher depending-on the patient's global response.

Memantine

Memantine is a cycloalkyl amine that has the chemical name 3,5-dimethyltricyclo[3.3.1.1$^{3,7}$]decan-1-amine. Procedures for the preparation of memantine are described in U.S. Pat. No. 3,391,142 and Stetter et al. *Ber.* 1960, 93, 226. The pharmacological properties are described in W. Wesemann et al. *Arzneimittel-Forsch.* 1983, 33, 1122 and P.-A. Fischer et al. *Arzneimittel-Forsch.* 1977, 27, 1487. The hydrochloride salt of memantin is marketed under the brandname AKATINOL®. The structure of memantine is presented below.

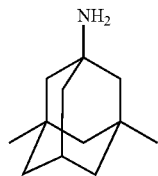

The size of a prophylactic or therapeutic dose of memantine in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 100 mg. Preferably, a daily dose range should be between about 1 mg to about 50 mg. Most preferably, a daily dose range should be between about 1 mg to about 25 mg. In certain embodiments, the daily dose range should be about 5, 10, 15, or 20 mg. In managing the patient, the therapy may be initiated at a lower dose, perhaps about 2 mg to about 3 mg and increased up to about 8 mg or higher depending-on the patient's global response.

Mesulergine

Mesulergine is an ergoline derivative that has the chemical name N'-(1,6-dimethylergolin-8α-yl)-N,N-dimethylsulfamide. The hydrochloride salt is a white solid that is soluble in water. Mesulergine has been used to treat Parkinson's Disease. The half-life of mesulergine in vivo is approximately 2 hr. The pharmacology and clinical results of treatment with mesulergine are reviewed by P. Galanopoulou and G. Gianakopoulos in *CNS Drug Reviews,* 1999, 5(3), 233. The structure of mesulergine is presented below.

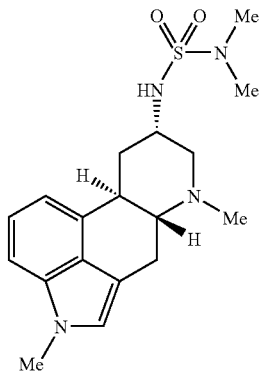 [SMILES: CN1C[C@@H](NS(=O)(=O)N(C)C)C[C@@H]2c3cccc4c3c(cn4C)C[C@H]21]

The size of a prophylactic or therapeutic dose of mesulergine in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 150 mg. Preferably, a daily dose range should be between about 1 mg to about 70 mg. Most preferably, a daily dose range should be between about 2 mg to about 25 mg. In certain embodiments, the daily dose range should be about 5, 10, 15, or 20 mg. In managing the patient, the therapy may be initiated at a lower dose, perhaps about 0.5 mg to about 1.5 mg and increased up to about 3 mg or higher depending-on the patient's global response.

Pergolide (PERMAX®)

Pergolide is an ergot derivative dopamine-receptor agonist. Procedures for the synthesis of pergolide are described in U.S. Pat. No. 4,166,182. A comprehensive description of pergolide can be found in Sprankle, D. J.; Jensen E. C. *Analytical Profiles of Drug Substances and Excipients* vol. 21, H. G. Brittain, Ed. (Academic Press, San Diego, 1992) pp 375-413. The dopominergic effects and other pharmacological properties of pergolide are described in R. W. Fuller et al. *Life Sci.* 1979, 24, 375 and Lemberger, L.; Crabtree, R. E. *Science* 1979, 205, 1151. The mesylate salt of pergolide is marketed under the tradename PERMAX® for the treatment of Parkinson's Disease. Pergolide mesylate is believed to exert its therapeutic effect by directly stimulating post-synaptic dopamine receptors in the nigrostriatal system. Procedures for preparing a stable pharmaceutical form of pergolide mesylate are described in U.S. Published Patent Application 20020054904. Pergolide has the chemical name 8(β)-8-[(methylthio)methyl]-6-propylergoline and the structure is presented below.

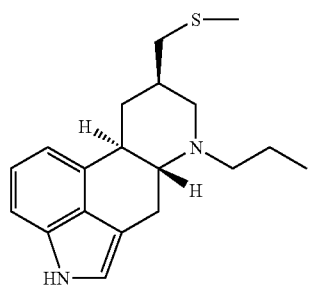 [SMILES: CCCN1C[C@H](CSC)C[C@@H]2c3cccc4[nH]cc(c34)C[C@H]21]

The size of a prophylactic or therapeutic dose of pergolide in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.05 mg to about 50 mg. Preferably, a daily dose range should be between about 0.05 mg to about 20 mg. Most preferably, a daily dose range should be between about 0.05 mg to about 5 mg. In certain embodiments, the daily dose range should be about 0.1, 0.25, 0.5, 1, 2, 3, or 4 mg. In managing the patient, the therapy may be initiated at a lower dose, perhaps about 0.05 mg to about 0.1 mg and increased up to about 3 mg or higher depending-on the patient's global response.

Piribedil

Piribedil is a piperazine derivative that is used to treat Parkinson's Disease. Procedures for the preparation of piribedil are described in U.S. Pat. No. 3,299,067. The compound's pharmacological properties are described in M. Laubie et al., *Eur. J. Pharmacol.* 1969, 6, 75. Piribedil has the chemical name 2-[4-(1,3-benzodioxol-5-ylmethyl)-1-piperazinyl]pyrimidine and the structure is presented below.

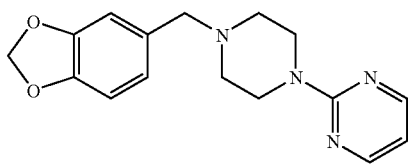 [SMILES: c1cnc(N2CCN(Cc3ccc4c(c3)OCO4)CC2)nc1]

The size of a prophylactic or therapeutic dose of piribedil in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 10 mg to about 750 mg. Preferably, a daily dose range should be between about 50 mg to about 500 mg. Most preferably, a daily dose range should be between about 100 mg to about 200 mg. In certain embodiments, the daily dose range should be about 125, 150, or 175 mg. In managing the patient, the therapy may be initiated at a lower dose, perhaps about 0.05 mg to about 0.1 mg and increased up to about 3 mg or higher depending-on the patient's global response.

Pramipexole (MIRAPEX®)

Pramipexole is a dopamine-$D_3$/$D_2$ receptor agonist known primarily its use in the treatment of schizophrenia and Parkinson's Disease. Procedures for the synthesis of racemic pramipexole are described in European Patent Application 186,087 and U.S. Pat. No. 4,886,812. The individual enantiomers of pramipexole may be obtained using the methods described in Schneider, C. S.; Mierau, J. *J. Med. Chem.* 1987, 30, 494. Pramipexole lowers the plasma level of prolactin. See German patent application DE 38 43 227. Further, it is known from German patent application DE 39 33 738 that pramipexole can be used to decrease abnormal high levels of thyroid stimulating hormone (TSH). Pramipexole has the chemical name 2-Amino-6-n-propyl-amino-4,5,6,7-tetrahydrobenzothiazole and the structure is presented below.

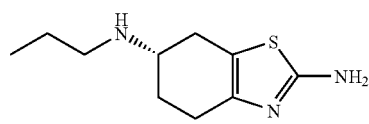

The pharmacological properties of pramipexole are described in Mierau, J.; Schingnitz, G. *Eur. J. Pharmacol.* 1992, 215, 161 and Schilling, J. C. et al. *Clin. Pharmacol. Ther.* 1992, 51, 541. Recently, pramipexole has been implicated for the treatment of restless-leg syndrome, depression, ADHD, and HIV dementia. See U.S. Pat. Nos. 6,194,445; 6,001,861; 6,255,329; and 6,410,579. See U.S. Published Patent Applications 20030036555 and 20030166696. The dihydrochloride salt of pramipexole is marketed under the brandname MIRAPEX® for the treatment of Parkinson's Disease.

The size of a prophylactic or therapeutic dose of pramipexole in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.1 mg to about 50 mg. Preferably, a daily dose range should be between about 0.1 mg to about 20 mg. Most preferably, a daily dose range should be between about 0.1 mg to about 5 mg. In certain embodiments, the daily dose range should be about 0.25, 0.5, 1, 2, 3, or 4 mg. In managing the patient, the therapy may be initiated at a lower dose, perhaps about 0.1 mg to about 0.2 mg and increased up to about 1 mg or higher depending-on the patient's global response. Patients with impaired renal function may suffer additional complications when administered pramipexole. In addition, patients that are pregnant are generally advised to not take pramipexole.

Quinagolide

Quinagolide is a $D_2$-receptor agonist. Procedures for the synthesis of quinagolide are described in U.S. Pat. No. 4,565,818 and *J. Med. Chem.* 1985, 28, 367. The pharmacological properties are described in Gaillard, R. C.; Brownell, *J. Life Sci.* 1988, 43, 1355 and C. Rasmussen et al. *Acta Endocrinol.* 1991, 125, 170. Quinagolide has the chemical name (3a,4α,10aβ)-(±)-N,N-diethyl-N'-(1,2,3,4,4a,5,10,10a-octahydro-6-hydroxy-1-propylbenzo[g]quinolin-3-yl)sulfamide and the structure is presented below.

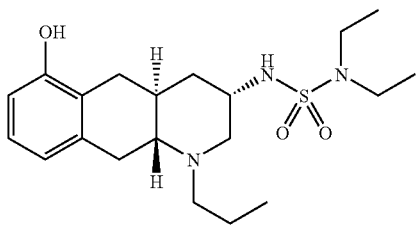 [SMILES: CCCN1C[C@@H](NS(=O)(=O)N(CC)CC)C[C@@H]2Cc3c(O)cccc3C[C@H]21]

The size of a prophylactic or therapeutic dose of quinagolide in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.01 mg to about 40 mg. Preferably, a daily dose range should be between about 0.05 mg to about 10 mg. Most preferably, a daily dose range should be between about 0.05 mg to about 2 mg. In certain embodiments, the daily dose range should be about 0.1, 0.25, 0.5, 0.75, 1, or 1.5 mg. In managing the patient, the therapy may be initiated at a lower dose, perhaps about 0.1 mg to about 0.2 mg and increased up to about 1 mg or higher depending-on the patient's global response. Patients with impaired renal function may suffer additional complications when administered pramipexole. In addition, patients that are pregnant are generally advised to not take pramipexole.

Ropinirole (REQUIP)

Ropinirole is a selective, non-ergoline dopamine $D_2$ receptor agonist. Procedures for the preparation of ropinirole are described in U.S. Pat. No. 4,452,808 and G. Gallagher Jr. et al. *J. Med. Chem.* 1985, 28, 1533. The pharmacological properties of ropinirole are described in R. J. Eden et al. *Pharmacol. Biochem. Behav.* 1991, 38, 147 and M. J. Vidailhet et al. *Lancet* 1990, 336, 316. Ropinirole is known to have antihypertensive properties and anti-anginal properties. U.S. Pat. Nos. 4,452,808 and 4,588,740. In addition, the hydrochloride salt of ropinirole is marketed under the brand name REQUIP for the treatment of Parkinson's Disease. Ropinirole has the chemical name 4-[2-(dipropylamino)ethyl]-1,3-dihydro-2H-indol-2-one and the structure is presented below.

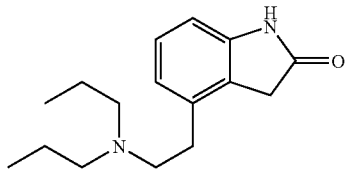 [SMILES: CCCN(CCC)CCc1cccc2c1CC(=O)N2]

The size of a prophylactic or therapeutic dose of ropinirole in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.1 mg to about 100 mg. Preferably, a daily dose range should be between about 0.2 mg to about 50 mg. Most preferably, a daily dose range should be between about 0.2 mg to about 10 mg. In certain embodiments, the daily dose range should be about 0.5, 1, 3, 5, 7, or 9 mg. In managing the patient, the therapy may be initiated at a lower dose, perhaps about 0.1 mg to about 0.5 mg and increased up to about 2 mg or higher depending on the patient's global response.

Roxindole

Roxindole is an indole derivative that is a dopamine $D_2$-receptor agonist. Procedures for the synthesis of roxindole are described in Hausberg, H.-H. et al. *Acta Pharm. Suec.* 1983, Suppl. 2, 213 and Bottcher, H. et al. *J. Med. Chem.* 1992, 35, 4020. The pharmacological properties of roxindole are described in C. A. Seyfried et al. *Eur. J. Pharmacol.* 1989, 160, 31 and Wiedemann, K.; Kellner, M. *Exp. Clin. Endrocrinol.* 1994, 102, 284. The dose, and perhaps the dose frequency, will also vary according to the age, body weight, and response of the individual patient. In general, the total daily dose ranges, for the conditions described herein, is from about 1 mg to about 900 mg. Preferably, a daily dose range should be between about 10 mg to about 200 mg. Roxindole has the chemical name 3-[4-(3,6-dihydro-4-phenyl-(2H)-pyridinyl)butyl]-1H-indol-5-ol and the structure is presented below.

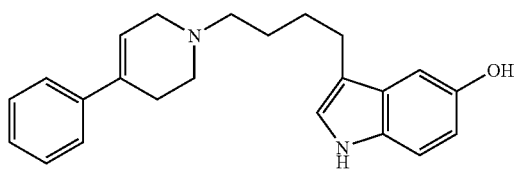 [SMILES: Oc1ccc2[nH]cc(CCCCN3CC=C(c4ccccc4)CC3)c2c1]

Talipexole

Talipexole is a dopamine $D_2$-receptor agonist. Procedures for the synthesis of talipexole are described in U.S. Pat. No. 3,804,849. The pharmacological properties of talipexole are described in P. A. Johansen et al. *Life Sci.* 1988, 43, 515 and Y. Mizuno et al. *Drug Invest.* 1993, 5, 186. The dihydrochloride salt of talipexole marketed under the brandname DOMIN® for the treatment of Parkinson's Disease. The dose, and perhaps the dose frequency, will also vary according to the age, body weight, and response of the individual patient. In general, the total daily dose ranges, for the conditions described herein, is from about 1 mg to about 900 mg. Preferably, a daily dose range should be between about 10 mg to about 200 mg. Talipexole has the chemical name 5,6,7,8-tetrahydro-6-(2-propenyl)-4H-thiazolo[4,5-d]azepin-2-amine and the structure is presented below.

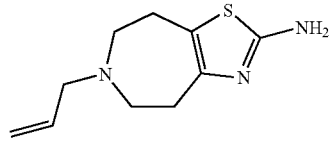

Sedative Agents

Racemic Zopiclone

Zopiclone is the first of a chemically distinct class of hypnotic and anxiolytic compounds that offers a psychotherapeutic profile of efficacy and side effects similar to the benzodiazepines. This class of compounds, the cyclopyrrolones, appears to cause less residual sedation and slowing of reaction times than the benzodiazepines, and it offers the promise of an improved therapeutic index over benzodiazepines.

The pharmacology of zopiclone has been shown both preclinically and clinically to be characterized by five distinct elements. It is predominantly a hypnotic-sedative, offering significant activity on first treatment in the absence of respiratory or cardiac depression. Additionally, zopiclone is an anticonvulsant, and it further exhibits muscle relaxant, anti-aggressive, and anxiolytic activities.

The compound binds to the benzodiazepine receptor complex, or to a site linked closely to this receptor complex. (See Goa, K. L. and Heel, R. C. Drugs, 32:48-65, (1986); Brun, J. P., Pharmacology, Biochemistry and Behavior, 29:831-832, (1988); Julou, L. et al., Pharmacology, Biochemistry and Behavior, 23:653-659, (1985); Verma, A. and Snyder S. H., Annu. Rev. Pharmacol. Toxicol, 29:307-322, (1989). The central benzodiazepine receptor is a macromolecular complex that includes a site for the binding of gamma-aminobutyric acid (GABA), the inhibitory neurotransmitter, suggesting that benzodiazepines and chemically unrelated agonists including zopiclone may exert their effects by facilitating the synaptic effects of GABA. While it interacts with the benzodiazepine receptor, zopiclone apparently has minimal effects on memory, no interaction with alcohol, and little or no abuse or dependence potential.

The pharmacologic activity of zopiclone is predominantly that of a sedative or hypnotic, particularly at low doses. Accordingly, the drug may improve sleep in adults and geriatric patients with several types of sleep disorders, and situational, transient, primary, and secondary insomnia. Following a bedtime dose of zopiclone, there is minimal impairment of psychomotor skills and mental acuity the following morning. The drug is well absorbed from the stomach, and it is not highly bound to plasma proteins.

The racemic mixture of zopiclone is presently used outside the United States primarily as an hypnotic, improving sleep patterns in chronic insomniacs and providing sleep induction before surgical procedures in hospitalized patients.

Insomnia is characterized by difficulty in sleeping or disturbed sleep patterns. Insomnia may be of a primary nature with little apparent relationship to immediate somatic or psychic events, or secondary to some acquired pain, anxiety or depression. Where possible, treatment is directed to the underlying cause of the condition; hypnotic medication such as zopiclone is generally reserved for insomnia of emotional disturbances and for refractory cases due to more common causes. In these cases, zopiclone provides sedative-hypnotic effects from the first day of treatment, an activity that is maintained following subsequent doses over long treatment periods. There appears to be no diminution or potentiation of activity in adult or geriatric patients, and little or no effect on alertness and performance some ten hours following the bedtime dose. (Brun, J. P. *Pharmacology, Biochemistry and Behavior* 1988, 29, 831-832).

In addition, the racemic mixture of zopiclone may be useful in treating other disorders such as convulsive states like epilepsy. Seizure disorder or epilepsy represents a broad group of central nervous system disorders of function that are characterized by recurrent, sudden, often brief attacks, which may alter consciousness, motor activity, sensory phenomena, and autonomic responses, and which may prompt inappropriate behavior. Recurrent seizure patterns of either an idiopathic or symptomatic etiology are termed epilepsy. The most common form of these recurrent but transient episodes are convulsive seizures, which may include loss of consciousness, motor function and control, and which may produce tonic or clonic jerking of the extremities. Pharmacological treatment of epilepsy has been directed to control based on seizure type, rather than etiology. Accordingly, the convulsions have been grouped in broad but rather distinct types including Tonic-clonic (Grand Mal), Partial (Focal) seizures, psychomotor (Complex partial) seizures, pyknoepileptic or Absence (Petit Mal) and the less frequent Myoclonic seizures.

The binding of zopiclone at or near the benzodiazepine receptor complex suggests that the compound may facilitate the inhibitory action of the neurotransmitter GABA and therefore its synaptic effects. As stated above, benzodiazepine receptors, which can be located both within the central nervous system and peripherally (e.g., in the endocrine system), are comprised of macromolecular complexes characterized by sites for binding of the benzodiazepines, GABA, and zopiclone. The benzodiazepine receptor complex is further associated with, and interacts with, a transmembrane channel for chloride ion transport. The effect of zopiclone's interaction with the benzodiazepine receptor/GABA receptor/chloride channel complex is to cause GABA to inhibit cerebral neuronal discharge, presumably by increasing membrane conductance of chloride ion, thus stabilizing membrane potentials and dampening excitatory input. (See Meldrum, B. S., Brit. J. Clin. Pharm., 27 (suppl. 1): 3S-11S, (1989)). It is believed that through mediation of this process zopiclone may be useful in treating epilepsy and a number of other conditions in which GABA is believed to exert a physiologic role.

While the racemic mixture of zopiclone may be useful in the treatment of the above-described disorders, it has a low therapeutic index and also causes adverse effects. These adverse effects include, but are not limited to, the development of a bitter taste due to the salivary secretion of the drug, dry mouth, drowsiness, morning tiredness, headache, dizziness, impairment of psychomotor skills and related effects.

It has recently been discovered that by using optically pure or substantially optically pure (+) zopiclone yields an increase in the potency of therapeutic effect as compared to that found in the racemic mixture. In addition, utilizing the optically pure isomer of (+) zopiclone results in clearer dose-related definitions of efficacy, diminished adverse effects, and accordingly, an improved therapeutic index. Hence, it is generally more desirable to use the (+) isomer of zopiclone.

Eszopiclone

Eszopiclone (or (+)-Zopiclone or (S)-zopiclone) is a potent drug useful for the treatment of sleep disorders, convulsive disorders, and disorders that are affected by the binding of agonists to central nervous system or peripheral benzodiazepine receptors. Administration of isomerically pure or substantially isomerically pure (e.g., 90%, 95%, or 99% isomeric purity) (+)-zopiclone is generally preferred because this isomer possesses potent activity in treating sleep disorders while avoiding adverse effects including but not limited to drowsiness, next day effects, such as tiredness in the morning, inability to concentrate and headache.

Eszopiclone is a cyclopyrrolone that has the chemical name (+) 6-(5-chloro-pyri-2-dyl)-5-(4-methylpiperazin-1-yl) carbonyloxy-7-oxo-6,7-dihydro-5H-pyrrolo[3-4b] pyrazin or (+) 6-(5-chloro-2-pyridinyl)-6,7-dihydro-7-oxo-5H-pyrrolo[3,4b]pyrazin-5-yl 4-methylpiperazine-1-carboxylate. The chemical structure of zopiclone is shown below:

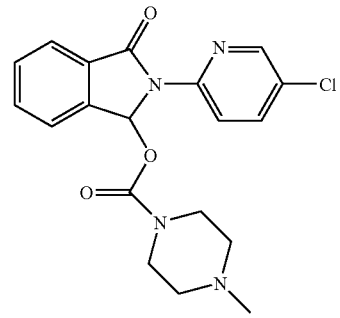 [SMILES: CN1CCN(C(=O)OC2c3ccccc3C(=O)N2c2ccc(Cl)cn2)CC1]

Eszopiclone is an optical isomer, the (+)-isomer, of the compound zopiclone, which is described in U.S. Pat. Nos. 6,319,926 and 6,444,673, and in Goa and Heel, [Drugs, 32:48-65 (1986)] and in U.S. Pat. Nos. 3,862,149 and 4,220,646. This isomer, which will hereinafter be referred to as eszopiclone, includes optically pure and the substantially optically pure (e.g., 90%, 95% or 99% optical purity) (+)-zopiclone isomer.

Racemic zopiclone is commercially available and can be made using various methods, such as those disclosed in U.S. Pat. Nos. 3,862,149 and 4,220,646. Eszopiclone may be prepared from racemic zopiclone using standard methods, such as chiral-phase chromatography, resolution of an optically active salt, stereoselective enzymatic catalysis by means of an appropriate microorganism, or asymmetric synthesis. U.S. Pat. No. 6,319,926 discloses methods for making eszopiclone, including resolution from racemic zopiclone by means of an optically active acid, such as D(+)-O,O'-dibenzoyltartaric acid.

Another method for making eszopiclone (or (S)-zopiclone) is by synthesis from racemic zopiclone (or (RS)-zopiclone) by chemical resolution via the D-malate salt as shown in the following synthesis schematic.

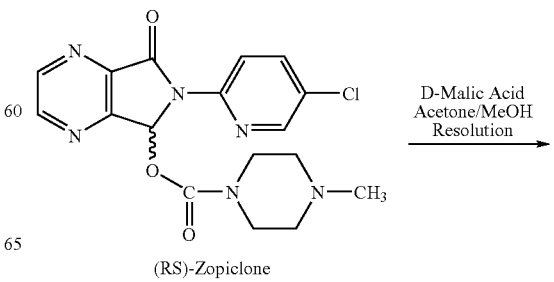

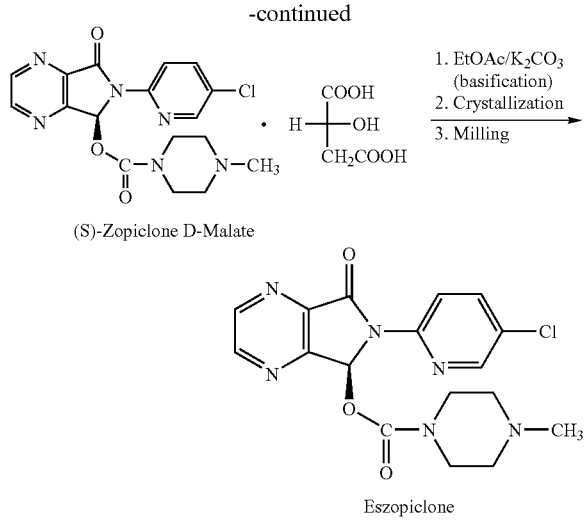

(S)-Zopiclone D-Malate

Eszopiclone

In the synthetic route shown above, (RS)-Zopiclone and D-malic acid are dissolved in a mixture of acetone and methanol to form (S)-zopiclone D-malate and (R)-zopiclone D-malate. The two diastereomeric salts are resolved in-situ by selective crystallization, filtration and rinsing to produce highly (S)-enriched zopiclone D-malate salt. In this process, the majority of (R)-zopiclone D-malate remains in the mother liquors. In this method, the use of an acetone/methanol co-solvent system results in a highly diastereoselective salt crystallization, and preferably, the co-solvent ratio used should be in the range of approximately 1.9/1 to 2.3/1 w/w acetone in methanol. Preferably, this stage of the process may also include cooling the reaction mixture during the isolation step to a temperature in the inclusive range of about 10° C. to 15° C., and washing or rinsing the wet cake obtained after filtration with cold solvent, such as cold methanol.

The resulting (S)-zopiclone D-malate salt is converted to optically pure eszopiclone free base by treatment with aqueous potassium carbonate and ethyl acetate, followed by phase separation and crystallization. In this process, once a solution of eszopiclone free-base is obtained, additional enantiomeric enrichment (typically 1 to 4%) can be achieved by crystallization from ethyl acetate of low water content. The water content can be controlled, e.g., by azeotropic distillation, and incorporating an in-process control of water content into the crystallization process can further improve the robustness of enantiomeric purity. Preferably, the water level during this step is 2% or less, more preferably 1% or less, and most preferably 0.6% or less.

Figure 2:
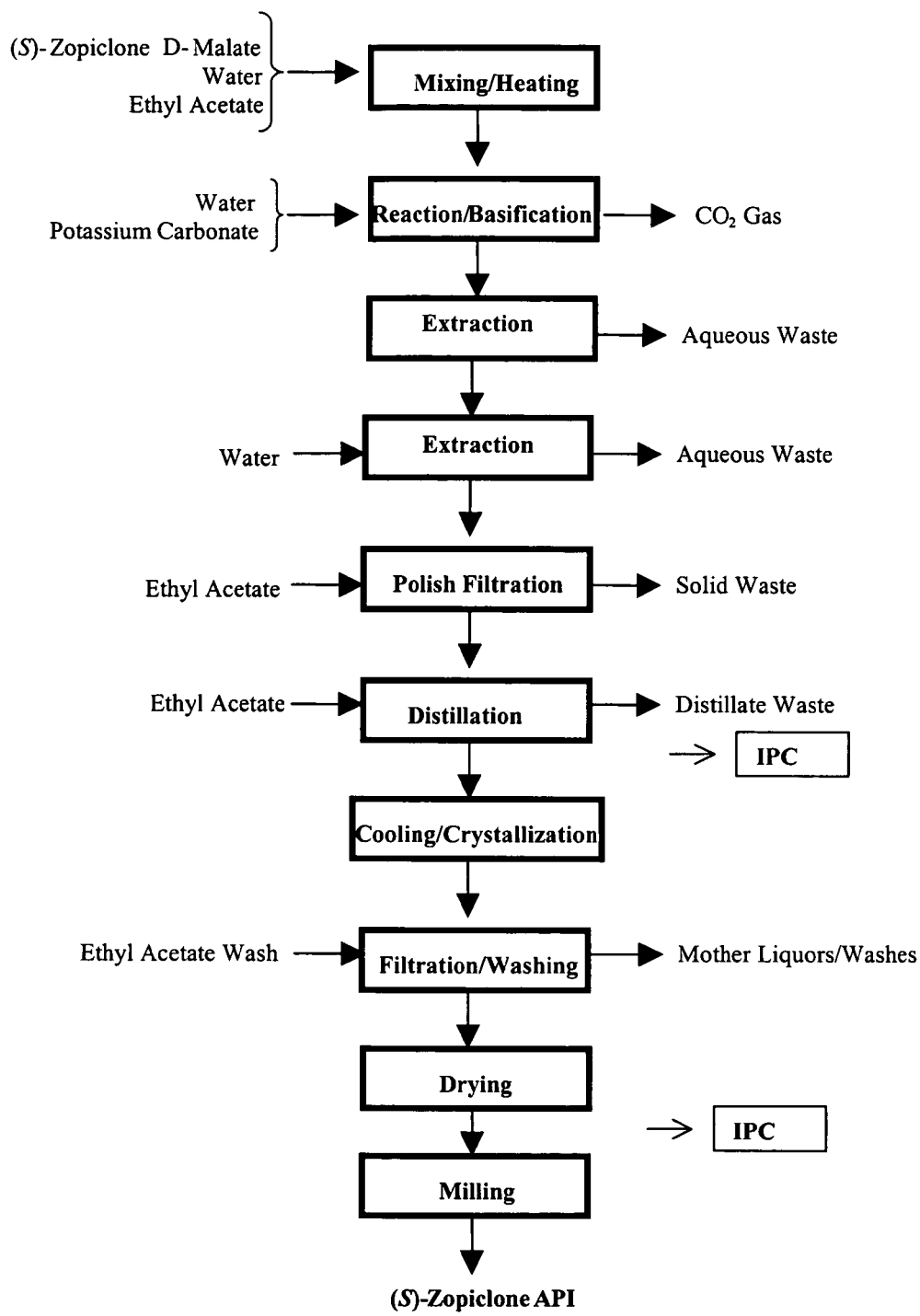
FIG. 2 depicts a schematic diagram of a method for preparing optically pure (S)-zopiclone as the free base (IPC=in-process control testing).

The resulting optically pure eszopiclone free base can then be milled to a desired size for use as an active ingredient in a pharmaceutical composition according to or for use in methods of the present invention. This two-stage process is depicted in the diagrams of FIGS. 1 and 2.

Eszopiclone possess potent activity in treating sleep disorders such as insomnia. Eszopiclone also possess potent activity in treating sleep disorders while avoiding the usual adverse effects including but not limited to drowsiness, next day effects tiredness in the morning, inability to concentrate and headache, which are associated with the administration of the racemic mixture of zopiclone. Eszopiclone also possess potent activity in treating convulsive disorders such as epilepsy while avoiding the adverse effects which are associated with the administration of the racemic mixture of zopiclone.

Additionally, compositions containing optically pure eszopiclone are useful in treating disorders that are affected by the binding of agonists to central nervous system and peripheral benzodiazepine receptors. Such disorders include but are not limited to aggressive behavior, muscle tension, behavioral disorders, depression, schizophrenia, and disorders associated with abnormal plasma hormone levels such as endocrine disorders. These compositions are useful in treating disorders that are affected by the binding of agonists to central nervous system and peripheral benzodiazepine receptors.

The size of a prophylactic or therapeutic dose of eszopiclone in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.25 mg to about 15 mg. Preferably, a daily dose range should be between about 0.5 mg to about 10 mg. Most preferably, a daily dose range should be between about 1.0 mg to about 5.0 mg. In managing the patient, the therapy may be initiated at a lower dose, perhaps about 0.5 mg to about 3 mg and increased up to about 5 mg or higher depending-on the patient's global response. It is further recommended that children and patients over 65 years, and those with impaired renal or hepatic function, initially receive low doses, and that they be titrated based on global response and blood level. It may be necessary to use dosages outside these ranges in some cases.

In the case where an oral composition is employed, a suitable dosage range for use is from about 0.25 mg to about 15.0 mg with, in the usual case, the lower doses serving more common insomnia, and the higher doses, presented in divided dosing, reserved for control of psychiatric disorders. Preferably, a dose range of between about 0.5 mg to about 10 mg is given as a once daily administration or in divided doses if required; most preferably, a dose range of from about 1.0 mg to about 5 mg is given, either as a once daily administration or in divided doses if required. Patients may be upward titrated from below to within this dose range to a satisfactory control of symptoms as appropriate.

The pharmacologic profile of hypnotic-sedative agents of the benzodiazepine class has been rather well established (Goodman and Gilman: The Pharmacological Basis of Therapeutics, 7th. Edition, Chapt. 17, 340-351, (1985), MacMillan Publishing Co., N.Y.) and has been extended to non-benzodiazepine agents of the cyclopyrrolone class (Bardone, M. C. et al., Abstract No. 2319, 7th. Int. Congr. Pharm. Paris, July, 1978, Pergamon Press, London; Julou, L. et al., Pharmacology, Biochemistry and Behavior, 23:653-659 (1985)). Accordingly, a variety of experimental models, which are rather well characterized (Julou, L. et al., ibid, 1985) can be used to characterize the various activities of zopiclone, its anticonvulsant, myorelaxant, anti-aggressive, and sedative-hypnotic activities. In an examination of each element of the pharmacologic profile, the activity of a pharmaceutical composition comprising zopiclone can be compared and contrasted with such pharmacologic standards as nitrazepam and diazepam, two benzodiazepine agents, in a variety of animal models. The dose (mg/kg) of each agent that is capable of inhibiting by 50% (the $ID_{50}$ or $ED_{50}$) an induced response in rodents, for example, provides the basis for comparison. Thus, pentylenetetrazole-induced convulsions, picrotoxin convulsions, and electrically-induced convulsions can be used to demonstrate the anti-convulsant activity of zopiclone (Haefely, W., Psychotropic Agents, eds. Hofmeister, F. and Stille, G., Springer Verlag, Berlin, Part 11, 12-262, (1981)).

Further, in the rat, in the amygdala kindled model of epilepsy, daily electrical stimulation of the amygdala induces a progressive increase of epileptic after discharge duration, with increasing epileptic behavioral symptoms, producing in some two weeks a generalized convulsive crisis. Presumably, previously ineffective stimuli have sensitized neuronal pathways, and it has been suggested that a similar mechanism may exist for the induction of an anxiety state in man after repeated stresses.

Similar models are available for determination of the myo-relaxant, anti-aggressive, and sedative-hypnotic activities of pharmaceutical compositions comprising zopiclone and its optically pure enantiomers in both mice and rats. (For review see Julou, L. et al., ibid, 1985.)

The acute toxicity of a pharmaceutical composition comprising zopiclone or eszopiclone can be determined in studies in which rats are administered at progressively higher doses (mg/kg) of pharmaceutical composition. That lethal dose which, when administered orally, causes death of 50% of the test animals, is reported as the $LD_{50}$.

The effects of a pharmaceutical composition on Psychomotor Behavior can be determined by measuring ten parameters (pinna reflex, spontaneous activity, palpebral size, startle response, touch response, reactivity, placing, righting reflex, exploration, and ataxia). Each parameter scores 2 points for normalcy for a total of 20 points×3 mice=60 points possible. Scores below 40 (<40) denote behavioral depression. Scores are determined before and after dosing with test sample. See Irwin, S., Psychopharrmacologia, 13:222-257 (1968).

| REFERENCE AGENTS ($ED_{100}$, mg/kg) | |
| --- | --- |
| chlordiazepoxide | 100 |
| chlorpromazine | 25 |
| clozapine | 25 |
| diazepam | 50 |
| glutethimide | 300 |
| haloperidol | 10 |
| meprobamate | 300 |
| pentobarbital | 100 |
| phenobarbital | 150 |
| reserpine | 50 |
| thioridazine | 50 |

(S)—N-Desmethylzopiclone

N-Desmethylzopiclone is a benzodiazepine receptor agonist that antagonizes muscarinic receptors. Procedures for the synthesis of racemic and optically pure (S)—N-desmethylzopiclone are described in U.S. Pat. Nos. 6,506,753; 6,458,791; and 6,339,086. N-desmethylzopiclone has been suggested for the treatment of a variety of diseases and disorders including insomnia, anxiety, muscle spasms, alcohol or drug addiction, and schizophrenia. The anxiolytic effects of optically pure (S)—N-desmethylzopiclone have been documented by J. N. Carlson and coworkers in Eur. J. Pharmacol. 2001, 415, 181. Administration of optically pure (S)—N-desmethylzopiclone is advantageous because this avoids long single-dose elimination half-life and adverse effects sometimes associated with racemic zopiclone. (S)—N-Desmethylzopiclone is a cyclopyrrolone that has the chemical name (S)-6-(5-chloro-pyri-2-dyl)-5-piperazinylcarbonyloxy-7-oxo-6,7-dihydro-5H-pyrrolo[3-4b]pyrazin. The chemical structure of (S)—N-desmethylzopiclone is shown below.

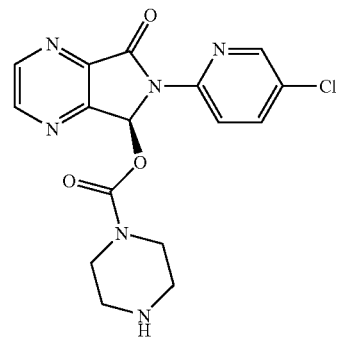 [SMILES: O=C(O[C@H]1c2nccnc2C(=O)N1c1ccc(Cl)cn1)N1CCNCC1]

The size of a prophylactic or therapeutic dose of optically pure (S)—N-desmethylzopiclone in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.1 mg to about 500 mg. Preferably, a daily dose range should be between about 0.5 mg to about 250 mg. Most preferably, a daily dose range should be between about 1 mg to about 200 mg. In certain embodiments, the daily dose range should be about 25, 50, 100, or 150 mg. In managing the patient, the therapy may be initiated at a lower dose, perhaps about 2 mg to about 5 mg and increased up to about 15 mg or higher depending-on the patient's global response.

It may be necessary to use dosages of the active ingredient outside the ranges disclosed herein in some cases, as will be apparent to those of ordinary skill in the art. Because elimination of metabolites from the bloodstream is dependant on renal and liver function, it is recommended that the total daily dose be reduced by at least about 50% in patients with moderate hepatic impairment, and that it be reduced by about 25% in patients with mild to moderate renal impairment. For patients undergoing hemodialysis, it is recommended that the total daily dose be reduced by about 5% and that the dose be withheld until the dialysis treatment is completed. Furthermore, it is noted that the clinician or treating physician will know how and when to interrupt, adjust, or terminate therapy in conjunction with individual patient response.

Indiplon

Indiplon is a potent sedative, anxiolytic and anti-convulsant agent, and possesses an improved profile of side effects, as compared to other benzodiazepine agents. Indiplon shows a reduced tolerance to sedation, a lowered potential for abuse and a reduced tendency to potentiate the deleterious effects of ethanol. In addition, Indiplon appears to be substantially devoid of next-day hangover effects and to have a considerably reduced anmesic potential compared to currently marketed sedative-hypnotic agents. The half-life of Indiplon in vivo is approximately 1.3 hours. Indiplon has the chemical name N-methyl-N-(3-{3-[2-thienylcarbonyl]-pyrazolo-[1,5-a]-pyrimidin-7-yl}-phenyl)acetamide and is represented by the formula below:

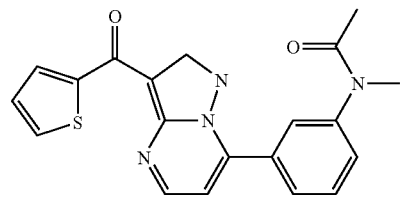 [SMILES: CC(=O)N(C)c1cccc(C2=CC=NC3=C(C(=O)c4cccs4)CNN23)c1]

Indiplon occurs as an off-white to yellow, non-free flowing powder with little static charge. The compound is lipid soluble (log D partition coefficient=1.73), and is soluble in water at approximately 20-30 µg/ml with a resulting pH of approximately 8.0. Indiplon may be prepared using chemical synthesis techniques known to those skilled in this field. For example, Indiplon may generally be made by the synthetic procedures disclosed in U.S. Pat. Nos. 4,521,422 and 4,900,836. These patents, particularly U.S. Pat. No. 4,521,422, disclose a genus encompassing certain aryl and heteroaryl[7-(aryl and heteroaryl)-pyrazolo[1,5-a]pyrimidin-3-yl]methanones.

The size of a prophylactic or therapeutic dose of Indiplon in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 75 mg. Preferably, a daily dose range should be between about 5 mg to about 50 mg. Most preferably, a daily dose range should be between about 10 mg to about 35 mg. In certain embodiments, the daily dose range should be about 10, 25, 30, or 35 mg. In managing the patient, the therapy may be initiated at a lower dose, perhaps about 2 mg to about 5 mg and increased up to about 10 mg or higher depending-on the patient's global response.

The mean plasma half-life of a sedative-hypnotic compound may be determined using well known techniques. Terminal half-life may be determined using standard pharmacokinetic calculations, such as those presented by Rolland and Tozer (Clinical Pharmacokinetics Concepts and Applications, $3^{rd}$ Ed., Chap. 3, 1995). in addition, software is commercially available which performs this calculation, such as the product sold under the tradename "WinNinlin™" (Prof. Ver. 1.5). This software calculates terminal plasma half-life ($t_{1/2}$) from the following relationship: "$t_{1/2}$=ln(2)/lambda.", wherein "ln(2)" is the natural log of 2 and "lambda." is the first order rate constant associated with the terminal (log-linear) portion of the plasma test compound concentration: time profile. This is estimated by linear regression analysis of the time vs. log concentration of the test compound.

The sedative-hypnotic effect of a compound may be readily established using, for example, standard tests that monitor the effects of a drug on motor activity, muscle relaxation and motor coordination (see, e.g., Beer et al., CNS Drug Reviews 3:207-224, 1997; Sanger et al., Eur. J. Pharmacol. 313:35-42, 1996, and references cited therein). In general, a sedative-hypnotic compound should have a statistically significant sedative effect within at least one, and preferably all, of the following assays:

(a) assays to detect a reduction in locomotor activity, as described by Sanger et al., European J Pharmacol. 313:35-42, 1996 and Beer et al., CNS Drug Reviews 3:207-224, 1997;
(b) assays to detect an increase in total sleep time, as determined by electroencephalographic (EEG) measures, as described in Beer et al., CNS Drug Reviews 3:207-224, 1997; and
(c) assays to detect a reduction in motor coordination, as defined by a reduced latency to remain on a rotating rod and/or a reduction in alertness, or vigilance (both assays as described by Sanger et al., European J Pharmacol. 313:35-42, 1996 and Beer et al., CNS Drug Reviews 3:207-224, 1997).

Zolpidem

Zolpidem is a hypnotic agent that is known to induce or maintain sleep. Zolpidem is an imidazopyridine having IUPAC chemical nomenclature N,N,6-trimethyl-2-(4-methylphenyl)-imidazo[1,2-s]pyridine-3-acetamide. The structure of zolpidem is presented below.

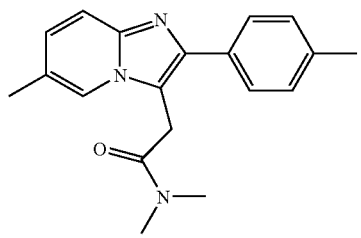

The zolpidem free base was disclosed generically in EP 50563 of Synthelabo. Zolpidem tartrate was subsequently disclosed in EP 251859 (U.S. Pat. No. 4,794,185). More recently, zolpidem has been suggested as useful in treating Parkinson's disease, parkinsonian symptoms, obsessive-compulsive disorder and certain forms of dementia in U.S. Pat. No. 5,891,891.

Zolpidem has been marketed as an immediate release tablet for oral application under the trade marks AMBIEN® and STILNOX®. In these commercial pharmaceutical dosage forms, zolpidem is present as a salt with L(+)tartaric acid wherein the molar ratio of zolpidem to tartaric acid is 2:1. This salt is conventionally called zolpidem hemitartrate but a more correct denomination thereof, which will be used hereinafter, is zolpidem tartrate. The European Pharmacopoeia, Monograph No. 1999:1280, states that zolpidem tartrate is characterized as a white or almost white crystalline powder, hygroscopic, slightly soluble in water, sparingly soluble in methanol, and practically insoluble in methylene chloride. Commercially available zolpidem tablets are conventional film coated tablets for immediate release of the active substance after ingestion and they contain 5 or 10 mg of zolpidem tartrate. The inactive ingredients are: lactose, microcrystalline cellulose, sodium starch glycolate, hydroxypropylmethylcellulose and magnesium stearate. The film coating layer consists of hydroxypropylmethylcellulose, polyethylene glycol and colorants.

Zolpidem is generally administrated orally by means of a tablet or other solid dosage form. Indeed pharmacokinetic and pharmacodynamic data show that zolpidem has both a rapid absorption and onset of hypnotic action. Its bioavailability is 70% following oral administration and demonstrates linear kinetics in the therapeutical dose range, which lies between 5 and 10 mg in conventional forms, peak plasma concentration is reached at between 0.5 and 3 hours, the elimination half-life is short, with a mean of 2.4 hours and a duration of action of up to 6 hours. Generally, the dosage of zolpidem is between 1 and 50 mg.

Traditionally, only immediate release dosage forms were developed which disintegrated rapidly in the gastrointestinal tract, dissolved in the fluid of the gastrointestinal tract and underwent systemic absorption, where zolpidem, can exert its pharmacological effect and induce sleep of the patient. More recently, new dosage forms have been developed which sustain release of zolpidem over a period compatible with the desired time of sleep and the time needed for elimination of the drug from the human body to a sufficiently low level. See U.S. Pat. Nos. 6,638,535 and 6,514,531.

The pharmacological effect of the zolpidem can be evaluated using the biological assays described in U.S. Pat. No. 4,382,938. For example, the toxicity of a compound can be determined on mice by intraperitoneal administration using LD 50 ranges from 500 to 1,000 mg/kg. In addition, the anxiolytic activity can be determined according to the eating test (R. J. Stephens, (1973), Brit. J. Pharmac., 49, 146 P). In this test, the doses which increases the food consumption of the mice vary from 0.1 to 10 mg/kg, administered intraperitoneally.

The activity of the compounds in the area of cerebral circulation can be determined in the test for the hypoxia caused by pressure reduction. Mice of the CD1 strain are kept in an oxygen-depleted atmosphere produced by creating a partial vacuum (190 mm of mercury, corresponding to 5.25% of oxygen). The survival time of the animals is noted. This time is increased by agents which are capable of assisting the oxygenation of tissues and in particular of the brain. The compounds studied are administered intraperitoneally in several doses, 10 minutes before the experiment. The percentage increases in the survival time, relative to the values obtained for control animals, are calculated. The mean active dose (MAD), that is to say the dose which increases the survival time by 100%, is determined graphically.

The anticonvulsant activity can be determined in accordance with the test for the antagonism towards the mortality induced by bicuculline in mice (P. Worms, H. Depoortere and K. G. Lloyd, (1979) Life Sci., 25, 607-614). The products to be studied are injected intraperitoneally, 30 minutes before the bicuculline (0.9 mg/kg, administered intravenously). With death being the criterion selected for this test, the percentage mortalities are noted for each batch, 2 hours after administration of the bicuculline (control batch: 100% mortality). For each product, the 50% active dose (AD 50 or the dose which protects 50% of the animals from the lethal effects of the bicuculline) is determined graphically.

The sedative or hypnotic activity can be determined by observing the action of the compounds on the EEG of curarised rats and also on the wake-sleep states in freely moving, implanted rats and cats (H. Depoortere, Rev. E.E.G. Neurophysiol., (1980) 10, 3, 207-214; L. M. Da Costa, H. Depoortere and R. Naquet, Rev. E.E.G. Neurophysiol., (1977), 7, 2, 158-164). In curarised rats, the products to be studied are injected intraperitoneally or orally at doses increasing from 0.1 to 30 mg/kg. In freely moving, implanted rats, the products to be studied were injected intraperitoneally or orally at a single dose ranging from 1 to 10 mg/kg. In freely moving, implanted cats, the products to be studied were injected intraperitoneally or orally at a single dose of 10 mg/kg.

The results of these various tests can be used to determine the anxiolytic, anti-anoxic, sleep-inducing, hypnotic and anticonvulsant properties of a pharmaceutical composition.

Zaleplon

Zaleplon (Wyeth-Ayerst), also known as "Sonata", is a nonbenzodiazepine recently approved by the FDA as sedative-hypnotic (see U.S. Pat. No. 4,626,538). Zaleplon is a pyrazolopyrimidine that has the chemical name N-[3-(3-cyanopyrazolo[1,5-a]pyrimidin-7-yl)phenyl]-N-ethylacetamide. Zaleplon is a white powder that has very low solubility in water and limited solubility in alcohol or propylene glycol. The structure of Zaleplon is given below.

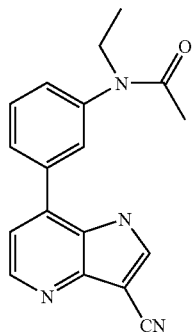 [SMILES: CCN(C(C)=O)c1cccc(-c2ccnc3c(C#N)c[nH]c23)c1]

Zaleplon binds to the gamma-aminobutyric acid benzodiazepine (GABA-BZ) receptor complex. Binding studies have revealed that Zaleplon binds selectively to the brain omega-1 receptor located on alpha subunit of the GABAA/chloride ion channel receptor complex. This interaction modulates the binding of t-butylbicyclophosphorothionate binding. Importantly, the pharmacological properties of benzodiazepines, e.g. sedative, anxiolytic, muscle relaxant, and anticonvulsive effects in animals, are linked to modulation of the GABA-BZ receptor chloride channel complex.

The pharmacokinetic profile of Zaleplon has been investigated in trials using a 60 mg single dose and once-daily administration of a 15 or 30 mg dose for up to 10 days. The data indicate that pharmacokinetics are proportional to the dose throughout the therapeutic range. In addition, Zaleplon does not accumulate in once-daily administration treatment regimes. Zaleplon is rapidly absorbed when administered orally; however, Zaleplon is subject to substantial presystemic metabolism resulting in only 30% bioavailability. The majority of the metabolism is attributed to an aldehyde oxidase which converts Zaleplon to 5-oxo-Zaleplon. Consequently, peak plasma concentrations following oral administration typically occur 1 hour after administration.

The size of a prophylactic or therapeutic dose of Zaleplon in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 50 mg. Preferably, a daily dose range should be between about 1 mg to about 25 mg. Most preferably, a daily dose range should be between about 5 mg to about 20 mg. In certain embodiments, the daily dose range should be about 5, 10, 15, or 20 mg. In managing the patient, the therapy may be initiated at a lower dose, perhaps about 2 mg to about 5 mg and increased up to about 10 mg or higher depending-on the patient's global response.

Generally, Zaleplon should be taken just prior to bedtime or immediately if a patient the patient has already gone to bed is having difficulty falling asleep. In certain instances the dose of Zaleplon should be adjusted in accord with diet or special needs of the patient. For example, the dosage of Zaleplon should be approximately 5 mg for elderly or debilitated patients whom are likely to be particularly sensitive to hypnotic medications. In addition, patients suffering from mild to moderate hepatic impairment should be administered only a 5 mg dose because systemic removal of drug is reduced in such patients.

Gaboxadol

Gaboxadol is a GABA-receptor agonist that has been shown to improve sleep-quality in both human and animal studies. Procedures for the preparation of gaboxadol have been described. U.S. Pat. No. 4,278,676; and P. Krogsgaard-Larsen, *Acta. Chem. Scand.* 1977, 31, 584. Gaboxadol, also known as THIP, is a crystalline, colorless solid that is soluble in water and methanol. The chemical name for gaboxadol is 4,5,6,7-tetrahydroisoxazolo[5,4-c]pyridin-3-ol. Gaboxadol is known to exist in two isomeric forms (Form A and Form B, shown below) and the term "gaboxadol" as used herein encompasses both forms separately, a mixture comprising both isomeric forms, and the pharmaceutically acceptable salts of any of them.

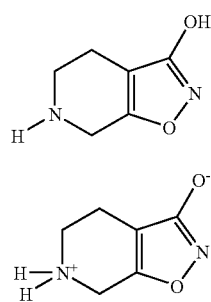

The GABA-receptor binding affinity and pharmacological properties of gaboxadol have been described. U.S. Pat. No. 4,278,676. In order to study the interactions of gaboxadol with the central GABA receptors in vitro, gaboxadol was tested in affinity binding experiments. See S. J. Enna and S. H. Snyder, *Brain Res.* 1975, 100, 81-97. The $IC_{50}$ value of gaboxadol was determined to be 0.13±0.005 µM based on experiments using five different concentrations of gaboxadol. Each experiment was conducted in triplicate and the $IC_{50}$ value was determined by logprobit analysis.

In order to study the interactions of gaboxadol with the central GABA receptors in vivo, gaboxadol was tested in microelectrophoretic experiments. See U.S. Pat. No. 4,278,676. Experiments were performed on lumbar dorsal horn interneurones and Renshaw cells of cats anaesthetized with pentobarbitone sodium. Gaboxadol was found to be relatively more potent than GABA on the basis of electrophoretic currents required to produce equal and submaximal inhibitions of the firing of the central neurones. The inhibitory action of gaboxadol on central neurones was reversibly antagonized by the specific GABA antagonist bicuculline methochloride (BMC). Interestingly, gaboxadol did not interact with the GABA uptake system at concentrations of $5 \times 10^4$ M, and it did not interact with the GABA metabolizing enzymes GABA: 2-oxo-glutarate aminotransferase and L-glutamate 1-carboxylase at concentrations of $10^{-3}$ M. Based on the above-mentioned experiments, gaboxadol is a specific and very potent GABA agonist. For additional information regarding the GABA receptor binding properties of gaboxadol, see: P. Krogsgaard-Larsen et al. *Nature* 1977, 268, 53.

The results from toxicity tests indicate that gaboxadol is less toxic than muscimol. The hydrobromide salt of gaboxadol has a $LD_{50}$ (mg/kg) of 80 (i.v.), 145 (i.p.), and >320 (p.o.) in mice. In comparison, muscimol has a $LD_{50}$ (mg/kg) of 7 (i.v.), 12 (i.p.), and 22 (p.o.) in mice. See U.S. Pat. No. 4,278,676.

Several studies have verified that gaboxadol can improve sleep quality. Lancel and coworkers conducted a double-blind, placebo-controlled study in healthy, elderly patients which revealed that oral administration of gaboxadol can increase sleep consolidation and the intensity of non-REM sleep. See Lancel, M.; Wetter, T. C.; Steiger, A.; Mathias, S. *Am. J. Physiol. Endocrinol. Metab.* 2001, 281, E130. In a post-nap sleep study, Mathias and coworkers found that gaboxadol facilitates falling asleep while increasing the total sleep time and promoting deep sleep. Mathias, S.; Steiger, A.; Lancel, M. *Psychopharmacology (Berl.)* 2001, 157, 299. For additional studies relating to therapeutic uses for gaboxadol see U.S. Pat. No. 5,929,065; Christensen et al. *Pharm. Weekbl., Scie. Ed.* 1982, 4, 145; and S. Korsgaard et al. *Arch. Gen. Psychiatry* 1982, 39, 1017.

The size of a prophylactic or therapeutic dose of gaboxadol will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 90 mg. Preferably, a daily dose range should be between about 2 mg to about 40 mg. Most preferably, a daily dose range should be between about 5 mg to about 30 mg. In certain embodiments, the daily dose range should be about 10, 15, 20, or 25 mg. In managing the patient, the therapy may be initiated at a lower dose, perhaps about 2 mg to about 4 mg and increased up to about 10 mg or higher depending-on the patient's global response.

Combination Therapy

One aspect of the present invention relates to combination therapy. This type of therapy is advantageous because the co-administration of active ingredients achieves a therapeutic effect that is greater than the therapeutic effect achieved by administration of only a single therapeutic agent. In a preferred embodiment, the co-administration of two or more therapeutic agents achieves a synergistic effect, i.e., a therapeutic affect that is greater than the sum of the therapeutic effects of the individual components of the combination.

The active ingredients that comprise a combination therapy may be administered together via a single dosage form or by separate administration of each active agent. In certain embodiments, the first and second therapeutic agents are administered in a single dosage form. The agents may be formulated into a single tablet, pill, capsule, or solution for parenteral administration and the like.

Alternatively, the first therapeutic agent and the second therapeutic agents may be administered as separate compositions, e.g., as separate tablets or solutions. The first active agent may be administered at the same time as the second active agent or the first active agent may be administered intermittently with the second active agent. The length of time between administration of the first and second therapeutic agent may be adjusted to achieve the desired therapeutic effect. In certain instances, the second therapeutic agent may be administered only a few minutes (e.g., 1, 2, 5, 10, 30, or 60 min) after administration of the first therapeutic agent. Alternatively, the second therapeutic agent may be administered several hours (e.g., 2, 4, 6, 10, 12, 24, or 36 hr) after administration of the first therapeutic agent. In certain embodiments, it may be advantageous to administer more than one dosage of the second therapeutic agent between administrations of the first therapeutic agent. For example, the second therapeutic agent may be administered at 2 hours and then again at 10 hours following administration of the first therapeutic agent. Alternatively, it may be advantageous to administer more than one dosage of the first therapeutic agent between administrations of the second therapeutic agent. Importantly, it is preferred that the therapeutic effects of each active ingredient overlap for at least a portion of the duration of each therapeutic agent so that the overall therapeutic effect of the combination therapy is attributable in part to the combined or synergistic effects of the combination therapy.

The dosage of the active agents will generally be dependent upon a number of factors including pharmacodynamic characteristics of each agent of the combination, mode and route of administration of active agent(s), the health of the patient being treated, the extent of treatment desired, the nature and kind of concurrent therapy, if any, and the frequency of treatment and the nature of the effect desired. In general, dosage ranges of the active agents often range from about 0.001 to about 250 mg/kg body weight per day. For a normal adult having a body weight of about 70 kg, a dosage in the range of from about 0.1 to about 25 mg/kg body weight is typically preferred. However, some variability in this general dosage range may be required depending upon the age and weight of the subject being treated, the intended route of administration, the particular agent being administered and the like. Since two or more different active agents are being used together in a combination therapy, the potency of each agent and the interactive effects achieved using them together must be considered. Importantly, the determination of dosage ranges and optimal dosages for a particular mammal is also well within the ability of one of ordinary skill in the art having the benefit of the instant disclosure.

In certain embodiments, it may be advantageous for the pharmaceutical combination to have a relatively large amount of the first component compared to the second component. In certain instances, the ratio of the first active agent to second active agent is 30:1, 20:1, 15:1, 10:1, 9:1, 8:1, 7:1, 6:1, or 5:1. In certain embodiments, it may be preferable to have a more equal distribution of pharmaceutical agents. In certain instances, the ratio of the first active agent to the second active agent is 4:1, 3:1, 2:1, 1:1, 1:2, 1:3, or 1:4. In certain embodiments, it may be advantageous for the pharmaceutical combination to have a relatively large amount of the second component compared to the first component. In certain instances, the ratio of the second active agent to the first active agent is 30:1, 20:1, 15:1, 10:1, 9:1, 8:1, 7:1, 6:1, or 5:1. Importantly, a composition comprising any of the above-identified combinations of first therapeutic agent and second therapeutic agent may be administered in divided doses 1, 2, 3, 4, 5, 6, or more times per day or in a form that will provide a rate of release effective to attain the desired results. In a preferred embodiment, the dosage form contains both the first and second active agents. In a more preferred embodiment, the dosage form only has to be administered one time per day and the dosage form contains both the first and second active agents.

For example, a formulation intended for oral administration to humans may contain from 0.1 mg to 5 g of the first therapeutic agent and 0.1 mg to 5 g of the second therapeutic agent, both of which are compounded with an appropriate and convenient amount of carrier material varying from about 5 to about 95 percent of the total composition. Unit dosages will generally contain between from about 0.5 mg to about 1500 mg of the first therapeutic agent and 0.5 mg to about 1500 mg of the second therapeutic agent. In a preferred embodiment, the dosage comprises 25 mg, 50 mg, 100 mg, 200 mg, 300 mg, 400 mg, 500 mg, 600 mg, 800 mg, or 1000 mg, etc., up to 1500 mg of the first therapeutic agent. In a preferred embodiment, the dosage comprises 25 mg, 50 mg, 100 mg, 200 mg, 300 mg, 400 mg, 500 mg, 600 mg, 800 mg, or 1000 mg, etc., up to 1500 mg of the second therapeutic agent.

The optimal ratios of the first and second therapeutic agent can be determined by standard assays known in the art. Thus, application of an equieffective dose substitution model and a curvilinear regression analysis utilizing all the data for the individual compounds and various dose ratios for the combinations can be used to establish the existence of unexpectedly enhanced activity of combinations of active agents, i.e., the resulting activity is greater than the activity expected from the sum of the activities of the individual components.

The toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of RT production from infected cells compared to untreated control as determined in cell culture. Such information can be used to more accurately determine useful doses in humans. Levels in plasma may be measured, for example, by high performance liquid chromatography (HPLC).

Synergism

The term "synergistic" refers to a combination which is more effective than the additive effects of any two or more single agents. A synergistic effect permits the effective treatment of a disease using lower amounts (doses) of either individual therapy. The lower doses result in lower toxicity without reduced efficacy. In addition, a synergistic effect can result in improved efficacy, e.g., improved antiviral activity. Finally, synergy may result in an improved avoidance or reduction of disease as compared to any single therapy.

Combination therapy often allows for the use of lower doses of the first therapeutic or the second therapeutic agent (referred to as "apparent one-way synergy" herein), or lower doses of both therapeutic agents (referred to as "two-way synergy" herein) than would normally be required when either drug is used alone. By using lower amounts of either or both drugs, the side effects associated with them are reduced.

In certain embodiments, the synergism exhibited between the second therapeutic agent and the first therapeutic agent is such that the dosage of the first therapeutic agent would be sub-therapeutic if administered without the dosage of the second therapeutic agent. In other embodiments, the present invention relates to a pharmaceutical composition comprising an therapeutically effective dose of a first therapeutic agent together with a dose of a second therapeutic agent effective to augment the therapeutic effect of the first therapeutic agent. Alternatively, the synergism exhibited between the second therapeutic agent and the first therapeutic agent is such that the dosage of the second therapeutic agent would be sub-therapeutic if administered without the dosage of the first therapeutic agent. In other embodiments, the present invention relates to a pharmaceutical composition comprising an therapeutically effective dose of a second therapeutic agent together with a dose of a first therapeutic agent effective to augment the therapeutic effect of the second therapeutic agent.

In certain preferred embodiments, the invention is directed in part to synergistic combinations of the first therapeutic agent in an amount sufficient to render a therapeutic effect together with a second therapeutic agent. For example, in certain embodiments a therapeutic effect is attained which is at least about 2 (or at least about 4, 6, 8, or 10) times greater than that obtained with the dose of the first therapeutic agent alone. In certain embodiments, the synergistic combination provides a therapeutic effect which is up to about 20, 30 or 40 times greater than that obtained with the dose of first therapeutic agent alone. In such embodiments, the synergistic combinations display what is referred to herein as an "apparent one-way synergy", meaning that the dose of second therapeutic agent synergistically potentiates the effect of the first therapeutic agent, but the dose of first therapeutic agent does not appear to significantly potentiate the effect of the second therapeutic agent.

In certain embodiments, the combination of active agents exhibit two-way synergism, meaning that the second therapeutic agent potentiates the effect of the first therapeutic agent, and the first therapeutic agent potentiates the effect of the second therapeutic agent. Thus, other embodiments of the invention relate to combinations of a second therapeutic agent and a first therapeutic agent where the dose of each drug is reduced due to the synergism between the drugs, and the therapeutic effect derived from the combination of drugs in reduced doses is enhanced. The two-way synergism is not always readily apparent in actual dosages due to the potency ratio of the first therapeutic agent to the second therapeutic agent. For instance, two-way synergism can be difficult to detect when one therapeutic agent displays much greater therapeutic potency relative to the other therapeutic agent.

The synergistic effects of combination therapy may be evaluated by biological activity assays. For example, the therapeutic agents are be mixed at molar ratios designed to give approximately equipotent therapeutic effects based on the $EC_{90}$ values. Then, three different molar ratios are used for each combination to allow for variability in the estimates of relative potency. These molar ratios are maintained throughout the dilution series. The corresponding monotherapies are also evaluated in parallel to the combination treatments using the standard primary assay format. A comparison of the therapeutic effect of the combination treatment to the therapeutic effect of the monotherapy gives a measure of the synergistic effect. Further details on the design of combination analyses can be found in B E Korba (1996) Antiviral Res. 29:49. Analysis of synergism, additivity, or antagonism can be determined by analysis of the aforementioned data using the CalcuSyn™ program (Biosoft, Inc.). This program evaluates drug interactions by use of the widely accepted method of Chou and Talalay combined with a statistically evaluation using the Monte Carlo statistical package. The data are displayed in several different formats including median-effect and dose-effects plots, isobolograms, and combination index [CI] plots with standard deviations. For the latter analysis, a CI greater than 1.0 indicates antagonism and a CI less than 1.0 indicates synergism.

Compositions of the invention present the opportunity for obtaining relief from moderate to severe cases of disease. Due to the synergistic and/or additive effects provided by the inventive combination of the first and second therapeutic agent, it may be possible to use reduced dosages of each of therapeutic agent. By using lesser amounts of other or both drugs, the side effects associated with each may be reduced in number and degree. Moreover, the inventive combination avoids side effects to which some patients are particularly sensitive.

Diseases and Disorders

Restless-Leg Syndrome

Restless-legs syndrome ("RLS") is a movement disorder characterized by uncomfortable sensations in the legs, which are worse during periods of inactivity, rest, or while sitting or lying down. Patients with the disorder describe the sensations as pulling, drawing, crawling, wormy, boring, tingling, pins and needles, prickly, itchy, and sometimes painful sensations that are usually accompanied by an overwhelming urge to move. These sensations usually occur in the calf area but may be felt anywhere from the thigh to the ankle. One or both legs may be affected, and in some, the sensations can also affect the arms. Most patients find movement or massaging provides temporary relief from the discomfort. Research suggests that RLS may also be related to periodic limb movement disorder (PLMD), another more movement disorder that is also identified as a parasomnia, which causes interrupted sleep, although while most patients with RLS also experience PLMD, the converse is not true. See Clark, *J. Am. Board Fam. Pract.*, 14(5):368-374 (2001).

Two forms of RLS appear to exist: The idiopathic and the uremic form. In this document both forms will be referred to as RLS. RLS, or restless-legs syndrome, is characterized by (1) a desire to move the legs, usually associated with paresthesias/dysesthesias, (2) motor restlessness, (3) worsening or exclusive presence of symptoms at rest (i.e. lying, sitting) with at least partial or temporary relief by activity, and (4) worsening of symptoms during the evening or night. According to the International RLS Study Group, these four minimal criteria already allow clinical diagnosis. While RLS is considered by some to be a sleep disorder, it is a movement disorder in which a person experiences unpleasant sensation in the legs, often described as creeping, tingling, pulling, or painful, and these sensations occur when the person with RLS lies down (e.g., to go to sleep) or sits for prolonged periods of time, such as at a desk, riding in a car, or watching a movie. RLS symptoms worsen during periods of relaxation and decreased activity. The evening and night hours tend to be more troublesome for RLS suffers.

Sensory and motor symptoms in RLS often result in severe sleep disturbances with prolonged sleep latency, decreased total sleep time with reduced or absent slow wave sleep and decreased sleep efficiency. RLS patients often sleep best toward the end of the night or during the morning hours. Because of less sleep at night, people with RLS may feel sleepy during the day on an occasional or regular basis. Almost all RLS patients present periodic leg movements (PLM) during sleep (PLMS) and also while being awake. The number of PLM and related parameters are considered to be a marker for the severity of RLS since PLM are frequently associated with nocturnal arousals or awakenings and if present during wakefulness may prevent patients from falling asleep. Therefore performing polysomnography is often needed to evaluate the efficacy of drug therapies. As a result of problems both while awake and prior to or during sleep, people with RLS may have difficulties with their job, social life, and recreational activites. RLS is reasonably common and always distressing.

Over the years, several treatments have been proposed for RLS. Typically treatments are grouped into four catagories: anticonvulsant drugs, benzodiazepines, opioids and dopaminergic agents. Several anticonvulsant drugs have been tested for use in treating RLS. Anticonvulsants appear to work by decreasing sensory disturbances (the unpleasant sensations) and the urge to move. These drugs are particularly effective for some, but not all, patients with marked daytime symptoms, particularly people who have pain syndromes associated with their RLS. Gabapentin (Neurontin) is the anticonvulsant that has shown the promise in treating the symptoms of RLS. Possible side effects of gabapentin include dizziness, sleepiness, fatigue, increased appetite, and unsteadiness. The sedative properties of gabapentin may impair the ability to operate heavy machinery, including a motor vehicle.

Several benzodiazepines, including clonazepam (KLONOPIN), nitrazepam, lorazepam and temazepam, have been used to treat RLS and sometimes improve the quality of nocturnal sleep. Benzodiazepines are central nervous system depressants that do not fully suppress RLS sensations or leg movements, but allow patients to obtain more sleep despite the problems. Some drugs in this group result in daytime drowsiness.

Opioids are narcotic analgesic (pain-killing) drugs and relaxing drugs that can suppress RLS and PLMS in some people especially those with severe and relentless symptoms of RLS. Some examples of medications in this category include codeine, propoxyphene (Darvon or Darvocet), oxycodone (Percocet, Tylox, Roxiprin), pentazocine (Talwin), hydrocodone (Vicodin), and methadone.

The therapeutic action of opioids was mentioned in the original description of RLS by Ekbom. Recently, this effect has been further documented in open clinical trials, see, Trzepacz, P. T.; Violette, E. J.; Sateia, M. J. *Am. J. Psychiatry* 1984, 141, 993-995 and Hening, W. A.; Walters, A.; Kavey, N.; Gidro-Frank, S.; Cote, L.; Fahn, S. *Neurology* 1986, 36, 1363. In these studies RLS was found to be reversible by naloxone, an opioid receptor antagonist. Opioids are potent suppressors of RLS and PLMS, but they carry the risk for abuse and the danger of addiction limit. Side effects and adverse reactions include dizziness, sedation, nausea, vomiting, constipation, hallucination, and headache. In severe cases, however, and especially in those undergoing hemodialysis, opiates may be an alternative treatment.

Dopaminergic drugs have produced some interesting results. Dopaminergic agents are drugs that are usually used to treat Parkinson's disease and in some cases may appear to provide some short term relief for some people with RLS. RLS is not a form of Parkinson's disease but is a distinct neurologic condition. Several studies have shown that L-dopa given with a peripheral carboxylase inhibitor at a 10:1 ratio is effective in treating RLS. See for example the following articles: Brodeur C, Montplaisir J, Marinier R, Godbout R., "Treatment of RLS and PMS with L-dopa: a double-blind controlled study," Neurology; 35:1845-1848 (1988). Montplaisir J, Godbout R, Poirier G, Bedard M. A., "Restless-legs syndrome and periodic movements in sleep: physiopathology and treatment with L-dopa," Clinical Neuropharmacology; 9:456-463 (1986). Von Scheele C, "Levodopa in restless-legs," Lancet; 2:426-427 (1986). Akpinar S., "Restless-legs syndrome treatment with dopaminergic drugs," Clinical Neuropharmacology; 10:69-79 (1987).

A controlled study using polysomnography (PSG) recordings in a double-blind design also showed that L-dopa administered twice at night produces a significant reduction of RLS occurring at bedtime and of PLMS throughout the night. Brodeur C, Montplaisir J, Marinier R, Godbout R., "Treatment of RLS and PMS with L-dopa: a double-blind controlled study," Neurology; 35:1845-1848 (1988). In most cases, L-dopa 100 mg, in conjunction with the decarboxylase inhibitor carbidopa 10 mg, completely suppresses RLS although a rebound (augmentation) of PLMS is often observed in the last part of the night. Montplaisir J, Godbout R, Poirier G, Bedard M. A., Clinical Neuropharmacology; 9:456-463 (1986). The two major side effects frequently seen in patients treated with L-dopa are: 1) a rebound of symptoms during daytime when patients are only treated at night; and 2) a single dose of L-dopa at bedtime decreases PLMS in the first third of the night but induces a rebound of these movements in the last third of the night when L-dopa is no longer effective. Similarly, the same study showed that when L-dopa treatment is repeated in the middle of the night, patients with severe cases may experience de novo paraesthesia and restlessness during the daytime.

Periodic-Limb-Movement Disorder

Periodic limb movements in sleep (PLMS), periodic limb movement disorder (PLMD) or nocturnal myoclonus involve involuntary (not consciously controlled) periodic episodes of repetitive limb movements during sleep that occur about every 20-40 seconds. The limb movements typically occur in the lower limbs or legs, but may occasionally also affect the arms, and can include without limitation, brief muscle twitches, jerking movements, or an upward flexing of the feet. Typically, the limb movements do not occur throughout the night or sleep cycle, but instead cluster in first portion of sleep or during non-REM sleep. The limb movements are much less common during REM sleep because the muscles are normally paralyzed during this phase of sleep to prevent a person from physically acting out their dreams.

PLMS or PLMD can result in a patient having various complaints about sleep, including without limitation, difficulty falling asleep, trouble in staying asleep or going back to sleep once they've awakened, or excessive daytime sleepiness. In many cases, the patient themselves may not report any difficulty with sleep, but their bed partner will report being disturbed by the movements, such as complaining of being hit or kicked by the patient during the night. The varied complaints about sleep that patients can have with PLMS or PLMD all arise from the same cause, but involve differences in the patients' timing and perception of the problem. For example, some patients may not be consciously aware of any sleep disturbance, but the many microarousals or brief awakenings during the night do disturb sleep and cause excessive daytime sleepiness. In other situations, limb movements occurring immediately after a patient falls asleep may awaken them before they realize they have fallen asleep, leading the patient to perceive that they have difficulty falling asleep.

Compositions of the Invention

One aspect of the present invention relates to a pharmaceutical composition, comprising a sedative agent and a dopamine-receptor agonist; wherein said sedative agent is selected from the group consisting of racemic zopiclone, optically pure (S)-zopiclone, optically pure (S)—N-desmethylzopiclone, indiplon, zolpidem, zaleplon, and gaboxadol or a pharmaceutically acceptable salt, solvate, or hydrate of any of them; and said dopamine-receptor agonist is selected from the group consisting of amantadine, apomorphine, bromocriptine, cabergoline, carmoxirole, optically pure (S)-didesmethylsibutramine, dopexamine, fenoldopam, ibopamine, lergotrile, lisuride, memantine, mesulergine, pergolide, piribedil, pramipexole, quinagolide, ropinirole, roxindole, and talipexole or a pharmaceutically acceptable salt, solvate, or hydrate of any of them.

In certain embodiments, the present invention relates to the aforementioned pharmaceutical composition, wherein said sedative agent is selected from the group consisting of optically pure (S)-zopiclone and optically pure (S)—N-desmethylzopiclone or a pharmaceutically acceptable salt, solvate, or hydrate of either of them.

In certain embodiments, the present invention relates to the aforementioned pharmaceutical composition, wherein said sedative agent is optically pure (S)-zopiclone or a pharmaceutically acceptable salt, solvate, or hydrate thereof.

In certain embodiments, the present invention relates to the aforementioned pharmaceutical composition, wherein said dopamine-receptor agonist is selected from the group consisting of apomorphine, bromocriptine, cabergoline, optically pure (S)-didesmethylsibutramine, lisuride, pergolide, pramipexole, and ropinirole or a pharmaceutically acceptable salt, solvate, or hydrate of any of them.

In certain embodiments, the present invention relates to the aforementioned pharmaceutical composition, wherein said dopamine-receptor agonist is optically pure (S)-didesmethylsibutramine or a pharmaceutically acceptable salt, solvate, or hydrate thereof.

In certain embodiments, the present invention relates to the aforementioned pharmaceutical composition, wherein said sedative agent is optically pure (S)-zopiclone or optically pure (S)—N-desmethylzopiclone or a pharmaceutically acceptable salt, solvate, or hydrate thereof; and said dopamine-receptor agonist is optically pure (S)-didesmethylsibutramine or a pharmaceutically acceptable salt, solvate, or hydrate thereof.

In certain embodiments, the present invention relates to the aforementioned pharmaceutical composition, wherein said sedative agent is optically pure (S)-zopiclone or a pharmaceutically acceptable salt, solvate, or hydrate thereof; and said dopamine-receptor agonist is optically pure (S)-didesmethylsibutramine or a pharmaceutically acceptable salt, solvate, or hydrate thereof.

In certain embodiments, the present invention relates to an aforementioned pharmaceutical composition, wherein said pharmaceutical composition further comprises at least one pharmaceutically acceptable carrier.

Another aspect of the present invention relates to a pharmaceutical composition consisting essentially of a sedative agent, a dopamine-receptor agonist, and at least one pharmaceutically acceptable carrier; wherein said sedative agent is selected from the group consisting of racemic zopiclone, optically pure (S)-zopiclone, optically pure (S)—N-desmethylzopiclone, indiplon, zolpidem, zaleplon, and gaboxadol or a pharmaceutically acceptable salt, solvate, or hydrate of any of them; and said dopamine-receptor agonist is selected from the group consisting of amantadine, apomorphine, bromocriptine, cabergoline, carmoxirole, optically pure (S)-didesmethylsibutramine, dopexamine, fenoldopam, ibopamine, lergotrile, lisuride, memantine, mesulergine, pergolide, piribedil, pramipexole, quinagolide, ropinirole, roxindole, and talipexole or a pharmaceutically acceptable salt, solvate, or hydrate of any of them.

In certain embodiments, the present invention relates to the aforementioned pharmaceutical composition, wherein said sedative agent is selected from the group consisting of optically pure (S)-zopiclone and optically pure (S)—N-desmethylzopiclone or a pharmaceutically acceptable salt, solvate, or hydrate of either of them.

In certain embodiments, the present invention relates to the aforementioned pharmaceutical composition, wherein said sedative agent is optically pure (S)-zopiclone or a pharmaceutically acceptable salt, solvate, or hydrate thereof.

In certain embodiments, the present invention relates to the aforementioned pharmaceutical composition, wherein said dopamine-receptor agonist is selected from the group consisting of apomorphine, bromocriptine, cabergoline, optically pure optically pure (S)-didesmethylsibutramine, lisuride, pergolide, pramipexole, and ropinirole or a pharmaceutically acceptable salt, solvate, or hydrate of any of them.

In certain embodiments, the present invention relates to the aforementioned pharmaceutical composition, wherein said dopamine-receptor agonist is optically pure (S)-didesmethylsibutramine or a pharmaceutically acceptable salt, solvate, or hydrate thereof.

In certain embodiments, the present invention relates to the aforementioned pharmaceutical composition, wherein said sedative agent is optically pure (S)-zopiclone or optically pure (S)—N-desmethylzopiclone or a pharmaceutically acceptable salt, solvate, or hydrate thereof; and said dopamine-receptor agonist is optically pure (S)-didesmethylsibutramine or a pharmaceutically acceptable salt, solvate, or hydrate thereof.

In certain embodiments, the present invention relates to the aforementioned pharmaceutical composition, wherein said sedative agent is optically pure (S)-zopiclone or a pharmaceutically acceptable salt, solvate, or hydrate thereof; and said dopamine-receptor agonist is optically pure (S)-didesmethylsibutramine or a pharmaceutically acceptable salt, solvate, or hydrate thereof.

Methods of the Invention

One aspect of the present invention relates to a method of treating a patient suffering from restless-leg syndrome or periodic-limb-movement disorder, comprising the step of:

co-administering to a patient in need thereof a therapeutically effective amount of a sedative agent and a dopamine-receptor agonist; wherein said sedative agent is selected from the group consisting of racemic zopiclone, optically pure (S)-zopiclone, optically pure (S)—N-desmethylzopiclone, indiplon, zolpidem, zaleplon, and gaboxadol or a pharmaceutically acceptable salt, solvate, or hydrate of any of them; and said dopamine-receptor agonist is selected from the group consisting of amantadine, apomorphine, bromocriptine, cabergoline, carmoxirole, optically pure (S)-didesmethylsibutramine, dopexamine, fenoldopam, ibopamine, lergotrile, lisuride, memantine, mesulergine, pergolide, piribedil, pramipexole, quinagolide, ropinirole, roxindole, and talipexole or a pharmaceutically acceptable salt, solvate, or hydrate of any of them.

In certain embodiments, the present invention relates to the aforementioned method, wherein said sedative agent is selected from the group consisting of optically pure (S)-zopiclone and optically pure (S)—N-desmethylzopiclone or a pharmaceutically acceptable salt, solvate, or hydrate of either of them.

In certain embodiments, the present invention relates to the aforementioned method, wherein said sedative agent is optically pure (S)-zopiclone or a pharmaceutically acceptable salt, solvate, or hydrate thereof.

In certain embodiments, the present invention relates to the aforementioned method, wherein said dopamine-receptor agonist is selected from the group consisting of apomorphine, bromocriptine, cab ergo line, optically pure (S)-didesmethylsibutramine, lisuride, pergolide, pramipexole, and ropinirole or a pharmaceutically acceptable salt, solvate, or hydrate of any of them.

In certain embodiments, the present invention relates to the aforementioned method, wherein said dopamine-receptor agonist is optically pure (S)-didesmethylsibutramine or a pharmaceutically acceptable salt, solvate, or hydrate thereof.

In certain embodiments, the present invention relates to the aforementioned method, wherein said sedative agent is optically pure (S)-zopiclone or optically pure (S)—N-desmethylzopiclone or a pharmaceutically acceptable salt, solvate, or hydrate thereof; and said dopamine-receptor agonist is optically pure (S)-didesmethylsibutramine or a pharmaceutically acceptable salt, solvate, or hydrate thereof.

In certain embodiments, the present invention relates to the aforementioned method, wherein said sedative agent is optically pure (S)-zopiclone or a pharmaceutically acceptable salt, solvate, or hydrate thereof; and said dopamine-receptor agonist is optically pure (S)-didesmethylsibutramine or a pharmaceutically acceptable salt, solvate, or hydrate thereof.

Another aspect of the present invention relates to a method of treating a patient suffering from a sleep abnormality, comprising the step of:

co-administering to a patient in need thereof a therapeutically effective amount of a sedative agent and a dopamine-receptor agonist; wherein said sedative agent is selected from the group consisting of racemic zopiclone, optically pure (S)-zopiclone, optically pure (S)—N-desmethylzopiclone, indiplon, zolpidem, zaleplon, and gaboxadol or a pharmaceutically acceptable salt, solvate, or hydrate of any of them; and said dopamine-receptor agonist is selected from the group consisting of amantadine, apomorphine, bromocriptine, cabergoline, carmoxirole, optically pure (S)-didesmethylsibutramine, dopexamine, fenoldopam, ibopamine, lergotrile, lisuride, memantine, mesulergine, pergolide, piribedil, pramipexole, quinagolide, ropinirole, roxindole, and talipexole or a pharmaceutically acceptable salt, solvate, or hydrate of any of them.

In certain embodiments, the present invention relates to the aforementioned method, wherein said sedative agent is selected from the group consisting of optically pure (S)-zopiclone and optically pure (S)—N-desmethylzopiclone or a pharmaceutically acceptable salt, solvate, or hydrate of either of them.

In certain embodiments, the present invention relates to the aforementioned method, wherein said sedative agent is optically pure (S)-zopiclone or a pharmaceutically acceptable salt, solvate, or hydrate thereof.

In certain embodiments, the present invention relates to the aforementioned method, wherein said dopamine-receptor agonist is selected from the group consisting of apomorphine, bromocriptine, cabergoline, optically pure (S)-didesmethylsibutramine, lisuride, pergolide, pramipexole, and ropinirole or a pharmaceutically acceptable salt, solvate, or hydrate of any of them.

In certain embodiments, the present invention relates to the aforementioned method, wherein said dopamine-receptor agonist is optically pure (S)-didesmethylsibutramine or a pharmaceutically acceptable salt, solvate, or hydrate thereof.

In certain embodiments, the present invention relates to the aforementioned method, wherein said sedative agent is optically pure (S)-zopiclone or optically pure (S)—N-desmethylzopiclone or a pharmaceutically acceptable salt, solvate, or hydrate thereof; and said dopamine-receptor agonist is optically pure (S)-didesmethylsibutramine or a pharmaceutically acceptable salt, solvate, or hydrate thereof.

In certain embodiments, the present invention relates to the aforementioned method, wherein said sedative agent is optically pure (S)-zopiclone or a pharmaceutically acceptable salt, solvate, or hydrate thereof; and said dopamine-receptor agonist is optically pure (S)-didesmethylsibutramine or a pharmaceutically acceptable salt, solvate, or hydrate thereof.

In certain embodiments, the present invention relates to the aforementioned method, wherein said sleep abnormality is difficulty falling asleep, difficulty staying awake, or waking up too early.

Immediate/Sustained Release Combination Therapy Dosage Forms

The combination therapy may be formulated in an immediate release dosage form or a sustained release dosage form. In certain embodiments, the present invention relates to immediate release dosage forms of the first and second therapeutic agents. An immediate release dosage form may be formulated as a tablet or multiparticulate which may be encapsulated. Other immediate release dosage forms known in the art can be employed. In certain embodiments, the combination of therapeutic agents may be formulated to provide for an increased duration (sustained release) of therapeutic action. These formulations, at comparable daily dosages of conventional immediate release drug, are often associated with a lower incidence or severity of adverse drug reactions; and they can also be administered at a lower daily dose than conventional oral medication while maintaining therapeutic activity.

In certain embodiments, the combination therapy can be formulated to delivery the therapeutic agents at the same time or at separate times. In certain embodiments, the first and second therapeutic agents are administered via an oral solid dosage form that includes a sustained release carrier causing the sustained release of the first therapeutic agent, or both the first therapeutic agent and the second therapeutic agent when the dosage form contacts gastrointestinal fluid. The sustained release dosage form may comprise a plurality of substrates which include the drugs. The substrates may comprise matrix spheroids or may comprise inert pharmaceutically acceptable beads which are coated with the drugs. The coated beads are then preferably overcoated with a sustained release coating comprising the sustained release carrier. The matrix spheroid may include the sustained release carrier in the matrix itself; or the matrix may comprise a normal release matrix containing the drugs, the matrix having a coating applied thereon which comprises the sustained release carrier. In other embodiments, the oral solid dosage form comprises a tablet core containing the drugs within a normal release matrix, with the tablet c ore being coated with a sustained release coating comprising the sustained release carrier. In further embodiments, the tablet contains the drugs within a sustained release matrix comprising the sustained release carrier. In additional embodiments, the tablet contains the first therapeutic agent within a sustained release matrix and the second therapeutic agent coated into the tablet as an immediate release layer.

The term "sustained release" is defined for purposes of the present invention as the release of the therapeutic agent from the formulation at such a rate that blood (e.g., plasma) concentrations (levels) are maintained within the therapeutic range (above the minimum effective analgesic concentration or "MEAC") but below toxic levels over a period of time of about 12 hours or longer.

The first and second therapeutic agents can be formulated as a controlled or sustained release oral formulation in any suitable tablet, coated tablet or multiparticulate formulation known to those skilled in the art. The sustained release dosage form may optionally include a sustained released carrier which is incorporated into a matrix along with the active agents, or which is applied as a sustained release coating.

The sustained release dosage form may include the first therapeutic agent in sustained release form and second therapeutic agent in the sustained release form or in immediate release form. The first therapeutic agent may be incorporated into the sustained release matrix along with the second therapeutic agent; incorporated into the sustained release coating; incorporated as a separated sustained release layer or immediate release layer; or may be incorporated as a powder, granulation, etc., in a gelatin capsule with the substrates of the present invention. Alternatively, the sustained release dosage form may have the first therapeutic agent in the sustained release form and the second therapeutic agent in the sustained release form or immediate release form.

An oral dosage form according to the invention may be provided as, for example, granules, spheroids, beads, pellets (hereinafter collectively referred to as "multiparticulates") and/or particles. An amount of the multiparticulates which is effective to provide the desired dose of the therapeutic agents over time may be placed in a capsule or may be incorporated in any other suitable oral solid form. In one certain embodiments of the present invention, the sustained release dosage form comprises such particles containing or comprising the active ingredient, wherein the particles have diameter from about 0.1 mm to about 2.5 mm, preferably from about 0.5 mm to about 2 mm.

In certain embodiments, the particles comprise normal release matrixes containing the first therapeutic agent with the second therapeutic agent. These particles are then coated with the sustained release carrier in embodiments where the first therapeutic agent is immediately released, the first therapeutic agent may be included in separate normal release matrix particles, or may be co-administered in a different immediate release composition which is either enveloped within a gelatin capsule or is administered separately. In other embodiments, the particles comprise inert beads which are coated with the second therapeutic agent with the first therapeutic agents. Thereafter, a coating comprising the sustained release carrier is applied onto the beads as an overcoat.

The particles are preferably film coated with a material that permits release of the active agents at a sustained rate in an aqueous medium. The film coat is chosen so as to achieve, in combination with the other stated properties, a desired in vitro release rate. The sustained release coating formulations of the present invention should be capable of producing a strong, continuous film that is smooth and elegant, capable of supporting pigments and other coating additives, non-toxic, inert, and tack-free.

Coatings

The dosage forms of the present invention may optionally be coated with one or more materials suitable for the regulation of release or for the protection of the formulation. In one embodiment, coatings are provided to permit either pH-dependent or pH-independent release, e.g., when exposed to gastrointestinal fluid. A pH-dependent coating serves to release the first active agent, second active agent, or both in the desired areas of the gastro-intestinal (GI) tract, e.g., the stomach or small intestine, such that an absorption profile is provided which is capable of providing at least about twelve hours and preferably up to twenty-four hours of therapeutic benefit to a patient. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine. In certain embodiments, the first therapeutic agent is released in one area of the GI tract and the second therapeutic agent is released in a second area of the GI tract. In certain embodiments, the first and second therapeutic agents are released in nearly equal amounts at the same location in the GI tract.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like. Thus, one aspect of the present invention relates to a formulation wherein the first therapeutic agent is coated over the enteric coat and released into the stomach while the second therapeutic agent is protected by the enteric coating and is released further down the GI tract. Alternatively, one aspect of the present invention relates to a formulation wherein the second therapeutic agent is coated over the enteric coat and released into the stomach while the first therapeutic agent is protected by the enteric coating and is released further down the GI tract.

In certain preferred embodiments, the substrate (e.g., tablet core bead, matrix particle) containing the first therapeutic a gent (with or without the second therapeutic a gent) is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Alternatively, the invention relates to instances wherein the substrate (e.g., tablet core bead, matrix particle) containing the second therapeutic agent (with or without the first therapeutic agent) is coated with a hydrophobic material. Such formulations are described, e.g., in detail in U.S. Pat. Nos. 5,273,760 and 5,286,493. Other examples of sustained release formulations and coatings which may be used in accordance with the present invention include U.S. Pat. Nos. 5,324,351; 5,356,467, and 5,472,712.

Alkylcellulose Polymers

Cellulosic materials and polymers, including alkylcelluloses, provide hydrophobic materials well suited for coating the formulations according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

Acrylic Polymers

In other preferred embodiments of the present invention, the hydrophobic material comprising the controlled release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are copolymers of acrylic and methacrylic acid esters with a low content of quaternary ammonium groups. In order to obtain a desirable dissolution profile, it may be necessary to incorporate in a coating two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Rohm Tech, Inc. There are several different types of Eudragit®. For example, Eudragit® E is an example of a methacrylic acid copolymer which swells and dissolves in acidic media. Eudragit® L is a methacrylic acid copolymer which does not swell at about pH<5.7 and is soluble at about pH>6. Eudragit® does not swell at about pH<6.5 and is soluble at about pH>7. Eudragit® RL and Eudragit® RS are water swellable, and the amount of water absorbed by these polymers is pH-dependent, however, dosage forms coated with Eudragit® RL and RS are pH-independent.

In certain preferred embodiments, the acrylic coating comprises a mixture of two acrylic resin lacquers commercially available from Rohm Pharma under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

Plasticizers

In embodiments of the present invention where the coating comprises an aqueous dispersion of a hydrophobic material, the inclusion of an effective amount of a plasticizer in the aqueous dispersion of hydrophobic material will further improve the physical properties of the sustained release coating. For example, because ethylcellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

Processes for Preparing Coated Beads

When the aqueous dispersion of hydrophobic material is used to coat inert pharmaceutical beads such as nu pariel 18/20 beads, a plurality of the resultant stabilized solid controlled release beads may thereafter be placed in a gelatin capsule in an amount sufficient to provide an effective controlled release dose when ingested and contacted by an environmental fluid, e.g., gastric fluid or dissolution media.

The stabilized controlled release bead formulations of the present invention slowly release the therapeutically active agent, e.g., when ingested and exposed to gastric fluids, and then to intestinal fluids. The controlled release profile of the formulations of the invention can be altered, for example, by varying the amount of overcoating with the aqueous dispersion of hydrophobic material, altering the manner in which the plasticizer is added to the aqueous dispersion of hydrophobic material, by varying the amount of plasticizer relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with a therapeutically active agent are prepared, e.g., by dissolving the therapeutically active agent in water and then spraying the solution onto a substrate, for example, nu pariel 18/20 beads, using a Wuster insert. Optionally, additional ingredients are also added prior to coating the beads in order to assist the binding of the active agents to the beads, and/or to color the solution, etc. For example, a product which includes hydroxypropylmethylcellulose, etc. with or without colorant (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic controlled release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Pre-formulated aqueous dispersions of ethylcellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

The plasticized aqueous dispersion of hydrophobic material may be applied onto the substrate comprising the therapeutically active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the aqueous dispersion of hydrophobic material to obtain a predetermined controlled release of said therapeutically active agent when said coated substrate is exposed to aqueous solutions, e.g., gastric fluid, is preferably applied, taking into account the physical characteristics of the therapeutically active agent, the manner of incorporation of the plasticizer, etc. After coating with the hydrophobic material, a further overcoat of a film-former, such as Opadry®, is optionally applied to the beads. This overcoat is provided, if at all, in order to substantially reduce agglomeration of the beads.

The release of the therapeutically active agent from the controlled release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic materials such as hydroxypropylmethylcellulose.

The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain. The release-modifying agent may also comprise a semi-permeable polymer.

In certain preferred embodiments, the release-modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864. The passageway can have any shape such as round, triangular, square, elliptical, irregular, etc.

Matrix Bead Formulations

In other embodiments of the present invention, the controlled release formulation is achieved via a matrix having a controlled release coating as set forth above. The present invention may also utilize a controlled release matrix that affords in-vitro dissolution rates of the active agent within the preferred ranges and that releases the active agent in a pH-dependent or pH-independent manner. The materials suitable for inclusion in a controlled release matrix will depend on the method used to form the matrix.

For example, a matrix in addition to the first active agent and (optionally) the second active agent may include: (1) Hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting controlled release of the active agent and which melts (or softens to the extent necessary to be extruded) may be used in accordance with the present invention. (2) Digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes, and stearyl alcohol; and polyalkylene glycols.

The hydrophobic material is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamine copolymer, poly(methyl methacrylate), poly (methacrylic acid)(anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing.

Preferred hydrophobic materials are water-insoluble with more or less pronounced hydrophilic and/or hydrophobic trends. Preferably, the hydrophobic materials useful in the invention have a melting point from about 30 to about 200 C, preferably from about 45 to about 90 C. Specifically, the hydrophobic material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic materials having hydrocarbon backbones.

Suitable waxes include, for example, beeswax, glycowax, castor wax and carnauba wax. For purposes of the present invention, a wax-like substance is defined as any material which is normally solid at room temperature and has a melting point of from about 30 to about 100 C.

Suitable hydrophobic materials which may be used in accordance with the present invention include digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25 and 90 C. are preferred. Of the long chain hydrocarbon materials, fatty (aliphatic) alcohols are preferred in certain embodiments. The oral dosage form may contain up to 60% (by weight) of at least one digestible, long chain hydrocarbon.

In certain instances, a combination of two or more hydrophobic materials are included in the matrix formulations. If an additional hydrophobic material is included, it may be selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water soluble hydroxyalkyl cellulose, at least one $C_{12}$-$C_{36}$, preferably $C_{14}$-$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethylcellulose. The amount of the at least one hydroxyalkyl cellulose in the present oral dosage form will be determined, inter alia, by the precise rate of release desired for the therapeutic agent. The at least one aliphatic alcohol may be, for example, lauryl alcohol, myristyl alcohol or stearyl alcohol. In certain embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of release desired for the therapeutic agent. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., the at least one hydroxyalkyl cellulose or acrylic resin to the at least one aliphatic alcohol/polyalkylene glycol determines, to a considerable extent, the release rate of the active agent from the formulation. A ratio of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferred between 1,000 and 15,000 especially between 1,500 and 12,000. Another suitable controlled release matrix would comprise an alkylcellulose (especially ethyl cellulose), a $C_{12}$ to $C_{36}$ aliphatic alcohol and, optionally, a polyalkylene glycol. In another preferred embodiment, the matrix includes a pharmaceutically acceptable combination of at least two hydrophobic materials. In addition to the above ingredients, a controlled release matrix may also contain suitable quantities of other materials, e.g. diluents, lubricants, binders, granulating aids, colorants, flavorants and glidants that are conventional in the pharmaceutical art.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 0.1 per cent to about ninety-nine percent of active ingredient, preferably from about 5 per cent to about 70 per cent, most preferably from about 10 per cent to about 30 per cent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The therapeutic agent alone or on combination with other therapeutic agents can be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They can also be combined where desired with other active agents, e.g., other analgesic agents. For parenteral application, particularly suitable are oily or aqueous solutions, as well as suspensions, emulsions, or implants, including suppositories. Ampoules are convenient unit dosages. For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay release of the active ingredients. Formulations for oral use may also be presented as hard gelatin capsules wherein the active ingredient is mixed with an inert diluent.

Aqueous suspensions contain the above-identified combination of drugs and that mixture has one or more excipients suitable as suspending agents, for example pharmaceutically acceptable synthetic gums such as hydroxypropylmethylcellulose or natural gums. Oily suspensions may be formulated by suspending the above-identified combination of drugs in a vegetable oil or mineral oil. The oily suspensions may contain a thickening agent such as beeswax or cetyl alcohol. A syrup, elixir, or the like can be used wherein a sweetened vehicle is employed. Injectable suspensions may also be prepared, in which case appropriate liquid carriers, suspending agents and the like may be employed. It is also possible to freeze-dry the active compounds and use the obtained lyophilized compounds, for example, for the preparation of products for injection.

One aspect of combination therapy pertains to a method for providing effective therapeutic treatment in humans, comprising administering an effective or sub-therapeutic amount of a first therapeutic agent; and administering an effective amount of a second therapeutic agent in an amount effective to augment the therapeutic effect provided by said first therapeutic agent. The second therapeutic agent can be administered before, simultaneously with, or after administration of the first therapeutic agent, as long as the dosing interval of the second therapeutic agent overlaps with the dosing interval of the first therapeutic agent (or its therapeutic effect). In other words, according to the method of the present invention, in certain preferred embodiments the second therapeutic agent need not be administered in the same dosage form or even by the same route of administration as the first therapeutic agent. Rather, the method is directed to the surprising synergistic and/or additive benefits obtained in humans, when therapeutically effective levels of a first therapeutic agent have been administered to a human, and, prior to or during the dosage interval for the second therapeutic agent or while the human is experiencing the therapeutic effect, an effective amount of a second therapeutic agent to augment the therapeutic effect of the first therapeutic agent is administered. If the second therapeutic agent is administered prior to the administration of the first therapeutic agent, it is preferred that the dosage intervals for the two drugs overlap, i.e., such that the therapeutic effect over at least a portion of the dosage interval of the first therapeutic agent is at least partly attributable to the second therapeutic agent.

In an additional method of the invention, the surprising synergistic and/or additive benefits obtained in the patient are achieved when therapeutically effective levels of the second therapeutic agent have been administered to the patient, and, during the dosage interval for the second therapeutic agent or while the patient is experiencing the therapeutic effect by virtue of the administration of a second therapeutic agent, an effective amount of a first therapeutic agent to augment the therapeutic effect of the second therapeutic agent is administered.

Another aspect of combination therapy relates to an oral solid dosage form comprising an therapeutically effective amount of a first therapeutic agent together with an amount of a second therapeutic agent or pharmaceutically acceptable salt thereof which augments the effect of the first therapeutic agent.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc.

administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective a mount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The terms "treatment" or "treating" are intended to encompass also prophylaxis, therapy, and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Micelles

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Polymers

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins

Cyclodextrins are cyclic oligosaccharides, consisting of 6, 7 or 8 glucose units, designated by the Greek letter alpha., beta. or gamma., respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459, 731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426, 011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 μm in diameter; large unilamellar vesicles (LUVS) are typically larger than 0.05 μm Oligolamellar large vesicles and multilamellar vesicles have multiple, usually concentric, membrane layers and are typically larger than 0.1 μm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

Release Modifiers

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Processes for Preparing Matrix-Based Beads

In order to facilitate the preparation of a solid, controlled release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose and the active agent; (b) mixing the hydroxyalkyl cellulose containing granules with at least one $C_{12}$-$C_{36}$ aliphatic alcohol; and (c) optionally, compressing and shaping the granules. Preferably, the granules are formed by wet granulating the hydroxyalkyl cellulose/active agent with water. In a particularly preferred embodiment of this process, the amount of water added during tie wet granulation step is preferably between 1.5 and 5 times, especially between 1.75 and 3.5 times, the dry weight of the active agent.

In yet other alternative embodiments, a spheronizing agent, together with the active ingredient can be spheronized to form spheroids. Microcrystalline cellulose is preferred. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxypropylcellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a hydrophobic material such as (a) a wax, either alone or in admixture with a fatty alcohol; or (b) shellac or zein.

Melt Extrusion Matrix

Sustained release matrices can also be prepared via melt-granulation or melt-extrusion techniques. Generally, melt-granulation techniques involve melting a normally solid hydrophobic material, e.g. a wax, and incorporating a powdered drug therein. To obtain a sustained release dosage form, it may be necessary to incorporate an additional hydrophobic substance, e.g. ethylcellulose or a water-insoluble acrylic polymer, into the molten wax hydrophobic material. Examples of sustained release formulations prepared via melt-granulation techniques are found in U.S. Pat. No. 4,861,598.

The additional hydrophobic material may comprise one or more water-insoluble wax-like thermoplastic substances possibly mixed with one or more wax-like thermoplastic substances being less hydrophobic than said one or more water-insoluble wax-like substances. In order to achieve constant release, the individual wax-like substances in the formulation should be substantially non-degradable and insoluble in gastrointestinal fluids during the initial release phases. Useful water-insoluble wax-like substances may be those with a water-solubility that is lower than about 1:5,000 (w/w).

In addition to the above ingredients, a sustained release matrix may also contain suitable quantities of other materials, e.g., diluents, lubricants, binders, granulating aids, colorants, flavorants and glidants that are conventional in the pharmaceutical art. The quantities of these additional materials will be sufficient to provide the desired effect to the desired formulation. In addition to the above ingredients, a sustained release matrix incorporating melt-extruded multiparticulates may also contain suitable quantities of other materials, e.g. diluents, lubricants, binders, granulating aids, colorants, flavorants and glidants that are conventional in the pharmaceutical art in amounts up to about 50% by weight of the particulate if desired.

Specific examples of pharmaceutically acceptable carriers and excipients that may be used to formulate oral dosage forms are described in the Handbook of Pharmaceutical Excipients, American Pharmaceutical Association (1986).

Melt Extrusion Multiparticulates

The preparation of a suitable melt-extruded matrix according to the present invention may, for example, include the steps of blending the active agent, together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides sustained release of the therapeutically active agent for a time period of from about 8 to about 24 hours.

An optional process for preparing the melt extrusions of the present invention includes directly metering into an extruder a hydrophobic material, a therapeutically active agent, and an optional binder; heating the homogenous mixture; extruding the homogenous mixture to thereby form strands; cooling the strands containing the homogeneous mixture; cutting the strands into particles having a size from about 0.1 mm to about 12 mm; and dividing said particles into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For purposes of the present invention, the terms "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

In another preferred embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are also described in Remington's Pharmaceutical Sciences, (Arthur Osol, editor), 1553-1593 (1980).

In yet another preferred embodiment, the extrudate can be shaped into tablets as set forth in U.S. Pat. No. 4,957,681 (Klimesch, et. al.).

Optionally, the sustained release melt-extruded multiparticulate systems or tablets can be coated, or the gelatin capsule can be further coated, with a sustained release coating such as the sustained release coatings described above. Such coatings preferably include a sufficient amount of hydrophobic material to obtain a weight gain level from about 2 to about 30 percent, although the overcoat may be greater depending upon the physical properties of the particular active agent utilized and the desired release rate, among other things.

The melt-extruded unit dosage forms of the present invention may further include combinations of melt-extruded multiparticulates containing one or more of the therapeutically active agents disclosed above before being encapsulated. Furthermore, the unit dosage forms can also include an amount of an immediate release therapeutically active agent for prompt therapeutic effect. The immediate release therapeutically active agent may be incorporated, e.g., as separate pellets within a gelatin capsule, or may be coated on the surface of the multiparticulates after preparation of the dosage forms (e.g., controlled release coating or matrix-based). The unit dosage forms of the present invention may also contain a combination of controlled release beads and matrix multiparticulates to achieve a desired effect.

The sustained release formulations of the present invention preferably slowly release the therapeutically active agent, e.g., when ingested and exposed to gastric fluids, and then to intestinal fluids. The sustained release profile of the melt-extruded formulations of the invention can be altered, for example, by varying the amount of retardant, i.e., hydrophobic material, by varying the amount of plasticizer relative to hydrophobic material, by the inclusion of additional ingredients or excipients, by altering the method of manufacture, etc.

In other embodiments of the invention, the melt extruded material is prepared without the inclusion of the therapeutically active agent, which is added thereafter to the extrudate. Such formulations typically will have the therapeutically active agent blended together with the extruded matrix material, and then the mixture would be tableted in order to provide a slow release formulation. Such formulations may be advantageous, for example, when the therapeutically active agent included in the formulation is sensitive to temperatures needed for softening the hydrophobic material and/or the retardant material.

DEFINITIONS

For convenience, certain terms employed in the specification, examples, and appended claims are collected here.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as sedative agents or dopamine agonists), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

As used herein, the term "optically pure" means that an active ingredient (e.g., (+)- or (S)-zopiclone or (S)-DDMS) for use in the compositions or methods of the present invention contain a significantly greater proportion of the specified enantiomer in relation to the non-specified enantiomer. For example, optically pure (+)-zopiclone contains a significantly greater proportion of the (+)-enantiomer in relation to the (−)-enantiomer. In a preferred embodiment, compositions including the optically pure active ingredients contain at least 90% by weight of the specified enantiomer and 10% by weight or less of the non-specified enantiomer. More preferably, such compositions contain at least 95% by weight of the specified enantiomer and 5% by weight or less of the non-specified enantiomer. Even more preferably, such compositions contain at least 99% by weight of the specified enantiomer and 1% by weight or less of the non-specified enantiomer. These percentages are based upon the total amount of the active ingredient.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "antagonist" refers to a compound that binds to a receptor site, but does not cause any physiological changes.

The terms "inverse agonist" and "negative antagonist" and "neutral antagonist" refer to compounds that inhibit an unoccupied, but active receptor.

The term "patient" refers to a mammal in need of a particular treatment. In a preferred embodiment, a patient is a primate, canine, feline, or equine. In another preferred embodiment, a patient is a human.

The phrases "sleep disorders" or "sleep abnormality" refers to primary insomnia; secondary insomnia; situational insomnia; transient insomnia; short-term insomnia; chronic insomnia; acute insomnia; prolonged latency to sleep onset; difficulty falling asleep; difficulty staying asleep; sleep maintenance problems, including without limitation, frequent awakenings, an increase in time spent awake after initially falling asleep (wake time after sleep onset, or WASO), sleep fragmentation, transient microarousals, and unrefreshing sleep; increased time awake during the sleep period; waking up too early; and reduced total sleep time.

The term "solvate" refers to a pharmaceutically acceptable form of a specified compound, with one or more solvent molecules, that retains the biological effectiveness of such compound. Examples of solvates include compounds of the invention in combination with solvents such, for example, water (to form the hydrate), isopropanol, ethanol, methanol, dimethyl sulfoxide, ethyl acetate, acetic acid, ethanolamine, or acetone. Also included are formulations of solvate mixtures such as a compound of the invention in combination with two or more solvents.

For purposes of this invention, the chemical elements are identified in accordance with the Periodic Table of the Elements, CAS version, Handbook of Chemistry and Physics, 67th Ed., 1986-87, inside cover.

EXEMPLIFICATION

The invention now being generally described, it will be more readily understood by reference to the following examples, which are included merely for purposes of illustration of certain aspects and embodiments of the present invention, and are not intended to limit the invention.

Example 1

Synthesis of Racemic Didesmethylsibutramine

An exemplary method of preparing racemic didesmethylsibutramine free base ((R/S)-DDMS) is described below.

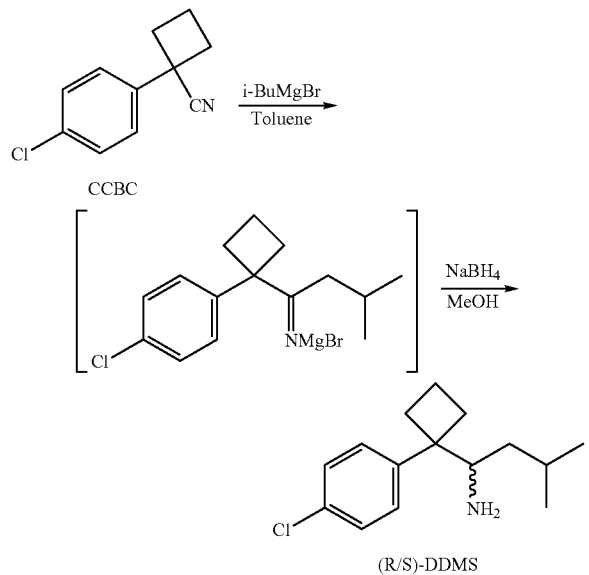

A 1 L three-necked round bottom flask was charged with isobutyl magnesium bromide (200 mL, 2.0 M in diethyl ether) and toluene (159 mL), and the resulting mixture was distilled to remove most of the ether. After the mixture was cooled to 20° C., CCBC (50.0 g) in toluene (45 mL) was added, and the resulting mixture was refluxed for 2-4 hours. The reaction mixture was then cooled to 0° C. and methanol (300 mL) was added to it, followed slowly by NaBH$_4$ (11 g). The resulting mixture was then added slowly to an aqueous HCl solution (365 mL, 2N) kept at 0° C., and the resulting mixture was warmed to room temperature with continual stirring. After separation of the organic phase, the aqueous phase was washed with toluene (200 mL). The combined organic phase were washed with water (200 mL) and concentrated to give (R/S)-DDMS (55 g, 85%). NMR (CDCl$_3$): $^1$H($\delta$), 0.6-0.8 (m, 1H), 0.8-1.0 (m, 6H), 1.1-1.3 (m, 1H), 1.6-2.6 (m, 7H), 3.0-3.3 (m, 1H), 7.0-7.6 (m, 4H). $^{13}$C($\delta$): 15.4, 21.5, 24.3, 24.7, 31.5, 31.9, 41.1, 50.73, 56.3, 127.7, 129, 131.6, 144.3.

Example 2

Synthesis of Racemic Didesmethylsibutramine•(D)-Tartrate

An exemplary method of preparing the (D)-tartrate salt of racemic didesmethylsibutramine ((R/S)-DDMS•(D)-TA) is described below. The (L)-tartrate salt of racemic didesmethylsibutramine ((R/S)-DDMS•(L)-TA) can be prepared in an analogous manner.

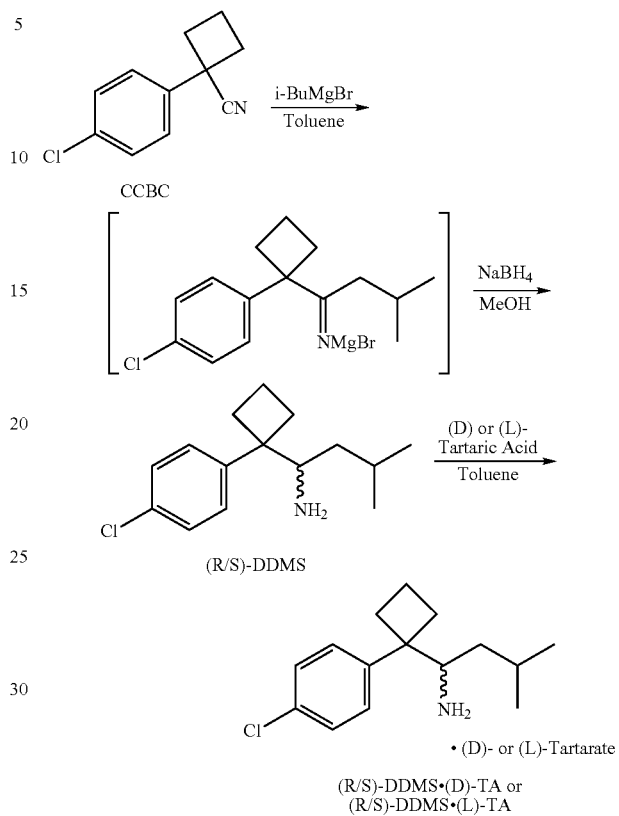

A mixture of racemic didesmethylsibutramine (15.3 g) and toluene (160 mL) was heated to 70-80° C. and (D)-tartaric acid (9.1 g) in water (20 mL) and acetone (10 mL) was added slowly. The resulting mixture was refluxed for 30 minutes, after which the water and acetone were removed by distillation. The resulting mixture was cooled to room temperature to provide a slurry which was then filtered. The resulting wet cake was washed two times with MTBE (20 mL×2) and dried to yield (R/S)-DDMS•(D)-TA (22.5 g, 98%). NMR (DMSO-d$_6$): $^1$H($\delta$), 0.6-0.92 (m, 6H), 0.92-1.1 (m, 1H), 1.1-1.3 (m, 1H), 1.5-1.8 (m, 2H), 1.8-2.1 (m, 1H), 2.1-2.4 (m, 3H), 2.4-2.6 (m, 1H), 3.4-3.6 (m, 1H), 3.9-4.2 (s, 2H), 6.4-7.2 (b, 6H, OH, COOH and NH$_2$), 7.3-7.6 (m, 4H). $^{13}$C($\delta$): 15.5, 21.1, 23.3, 23.7, 31.5, 37.7, 39.7, 54.5, 72.1, 128, 129.7, 131.3, 142.2, 174.6.

Example 3

Resolution of (S)-Didesmethylsibutramine•(L)-Tartrate

A method of isolating the (L)-tartrate salt of optically pure (S)-didesmethylsibutramine ((S)-DDMS•(L)-TA) from racemic didesmethylsibutramine free base is described below.

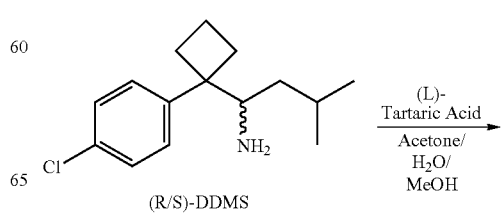

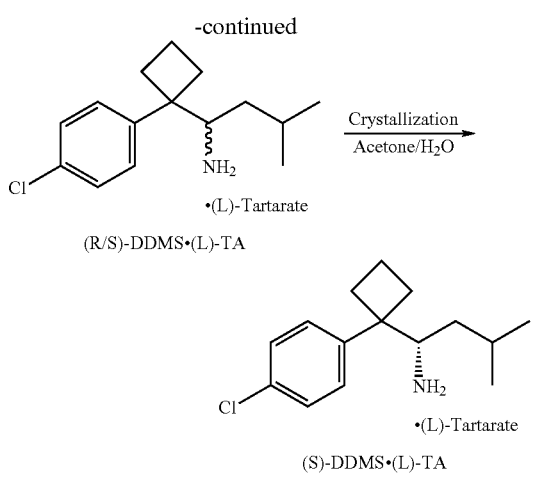

(R/S)-DDMS•(L)-TA (S)-DDMS•(L)-TA

Formation of (L)-Tartrate Salt of (S)-DDMS (R/S)-DDMS (20.5 g), acetone/water/methanol (350 mL, 1:0.13:0.7, v:v:v) and (L)-tartaric acid (12.2 g) were added to a 500 mL three-necked round bottom flask. The mixture was heated to reflux for 30 minutes and then cooled to 45° C. The reaction mixture was then seeded with (S)-DDMS•(L)-TA (10 mg and 99.7% ee) and stirred at 40-45° C. for 30 minutes. The mixture was cooled to room temperature and stirred for 1 hour. The resulting slurry was filtered to provide a wet cake, which was washed with cold acetone/water and dried to give 10.8 g (33.4%) of (S)-DDMS•(L) TA (89.7% ee).

Preparation of (L)-Tartate Salt of (S)-DDMS from Mother Liquor of (R)-DDMS•(D)-TA A solution of DDMS tartrate in acetone/water/methanol (mother liquor of (R)-DDMS•(D)-TA) was concentrated to remove acetone and methanol. The residue was treated with aqueous NaOH (3N, 150 mL) and extracted with ethyl acetate. The organic phase was washed with water (100 mL) and concentrated to give didesmethylsibutramine free base (45 g, 0.18 mol and 36% ee of (S)-isomer). The free amine was charged with (L)-tartric acid (53.6 g, 0.35 mol), acetone (600 mL), water (80 mL), and methanol (40 mL). The mixture was heated to reflux for 1 hour and then cooled to room temperature. The resulting slurry was filtered to provide a wet cake, which was then washed with cold acetone/water two times to give 26.7 g (56% based on (S)-didesmethylsibutramine) of (S)-DDMS•(L)-TA (96% ee).

Enrichment of (S)-DDMS•(L)-TA

A mixture of (S)-DDMS•(L)-TA (26.7 g) in acetonitrile/water (475 mL, 1:0.2, v:v) was refluxed for 1 hour and then cooled to room temperature. The resulting slurry was filtered and dried to give 17.4 g (65%) of (S)-DDMS•(L)-TA (99.9% ee; 99.94% chemical purity). NMR (DMSO-$d_6$): $^1$H ($\delta$), 0.7-0.9 (m, 6H), 0.9-1.05 (m, 1H), 1.1-1.3 (b, 1H), 1.52-1.8 (b, 2H), 1.84-2.05 (b, 1H), 2.15-2.4 (b, 3H), 2.4-2.6 (b, 1H), 3.65-3.68 (m, 1H), 4.0 (s, 2H), 6.7-7.3 (b, 6H from $NH_2$, OH and COOH), 7.1-7.6 (m, 4H). 13C($\delta$): 15.4, 21.5, 22.0, 22.2, 32.0, 32.2, 38.4, 49.0, 54.0, 72.8, 128.8, 130.0, 132.0, 143.0, 175.5.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A method of treating a patient suffering from restless-leg syndrome or periodic-limb-movement disorder, comprising the step of administering a single dosage form consisting of:
   (a) one or more pharmaceutically acceptable carriers;
   (b) eszopiclone;
   (c) a dopamine-receptor agonist selected from the group consisting of amantadine, apomorphine, bromocriptine, cabergoline, carmoxirole, dopexamine, fenoldopam, ibopamine, lergotrile, lisuride, memantine, mesulergine, pergolide, piribedil, pramipexole, quinagolide, ropinirole, roxindole, and talipexole or a pharmaceutically acceptable salt of any of them; and
   (d) optionally, a coating.

2. The method of claim 1, wherein said dopamine-receptor agonist is selected from the group consisting of apomorphine, bromocriptine, cabergoline, lisuride, pergolide, pramipexole, and ropinirole or a pharmaceutically acceptable salt of any of them.

* * * * *